US007827635B2

(12) United States Patent
Wang et al.

(10) Patent No.: US 7,827,635 B2
(45) Date of Patent: Nov. 9, 2010

(54) SUBJECT TABLE FOR ISOLATION ENVIRONMENT

(75) Inventors: Zhengyan Wang, N. Canton, OH (US); Steven J. Plummer, Hudson, OH (US); Jacin C. Barnes, Willowick, OH (US); Matthew D. Fleischhauer, Mentor, OH (US); Michael G. Ambrosia, Cleveland Heights, OH (US); Dennis K. Everett, Seven Hills, OH (US); Robert G. Henderson, Wickliffe, OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 234 days.

(21) Appl. No.: 11/845,199

(22) Filed: Aug. 27, 2007

(65) Prior Publication Data

US 2008/0173218 A1 Jul. 24, 2008

Related U.S. Application Data

(63) Continuation of application No. PCT/US2007/069838, filed on May 29, 2007.

(60) Provisional application No. 60/804,311, filed on Jun. 9, 2006.

(51) Int. Cl.
*A47B 13/00* (2006.01)

(52) U.S. Cl. .................. 5/601; 5/943; 378/20; 378/208

(58) Field of Classification Search .................... 5/601, 5/943; 378/209, 37, 195, 208, 20; 600/410
See application file for complete search history.

(56) References Cited

U.S. PATENT DOCUMENTS 3,937,993 A * 2/1976 Noodleman .................. 310/46

| | | | | |
|---|---|---|---|---|
| 4,545,571 A * | 10/1985 | Chambron | ...................... | 5/601 |
| 4,641,823 A * | 2/1987 | Bergman | .................. | 5/81.1 HS |
| 4,922,806 A * | 5/1990 | Newman et al. | ............. | 454/195 |
| 4,984,774 A * | 1/1991 | Zupancic et al. | ............... | 5/601 |
| 6,322,251 B1 * | 11/2001 | Ballhaus et al. | ............. | 378/209 |
| 6,381,780 B1 * | 5/2002 | Nose et al. | ...................... | 5/601 |
| 6,885,165 B2 * | 4/2005 | Henley et al. | ............... | 318/687 |
| 6,955,464 B1 | 10/2005 | Tybinkowski et al. | | |
| 7,167,739 B2 * | 1/2007 | Van De Rijdt et al. | ...... | 600/415 |

(Continued)

FOREIGN PATENT DOCUMENTS

| | | |
|---|---|---|
| DE | 1566654 | 8/1970 |
| DE | 19639975 C1 | 5/1998 |
| DE | 10049414 A1 | 5/2002 |
| DE | 102004007427 A1 | 9/2005 |
| DE | 102004008343 A1 | 9/2005 |
| EP | 0761166 A2 | 3/1997 |
| WO | WO 2005025423 A1 * | 3/2005 |

OTHER PUBLICATIONS

National Institute of Allergy and Infectious Deseases Fact Sheet, "Frequently Asked Questions: An Integrated Research Facility at Fort Detrick, Maryland" http://www.niaid.nih.gov/factsheets/detrick_qa.htm.

(Continued)

*Primary Examiner*—Robert G Santos
*Assistant Examiner*—Brittany M Wilson

(57) ABSTRACT

A subject loading system is provided for moving a subject disposed in an isolation zone into and out of a diagnostic system disposed outside the isolation zone. A tube extends away from the isolation zone. The tube has an inner volume open to the isolation zone and operatively coupled with the diagnostic system. An elongated subject support pallet is disposed in the isolation zone and dimensioned to fit into the tube. A base including a mechanical drive is disposed in the isolation zone and is configured to align the elongated subject support pallet with the tube and to move the elongated subject support pallet into and out of the tube.

29 Claims, 24 Drawing Sheets

U.S. PATENT DOCUMENTS

Figure 1:
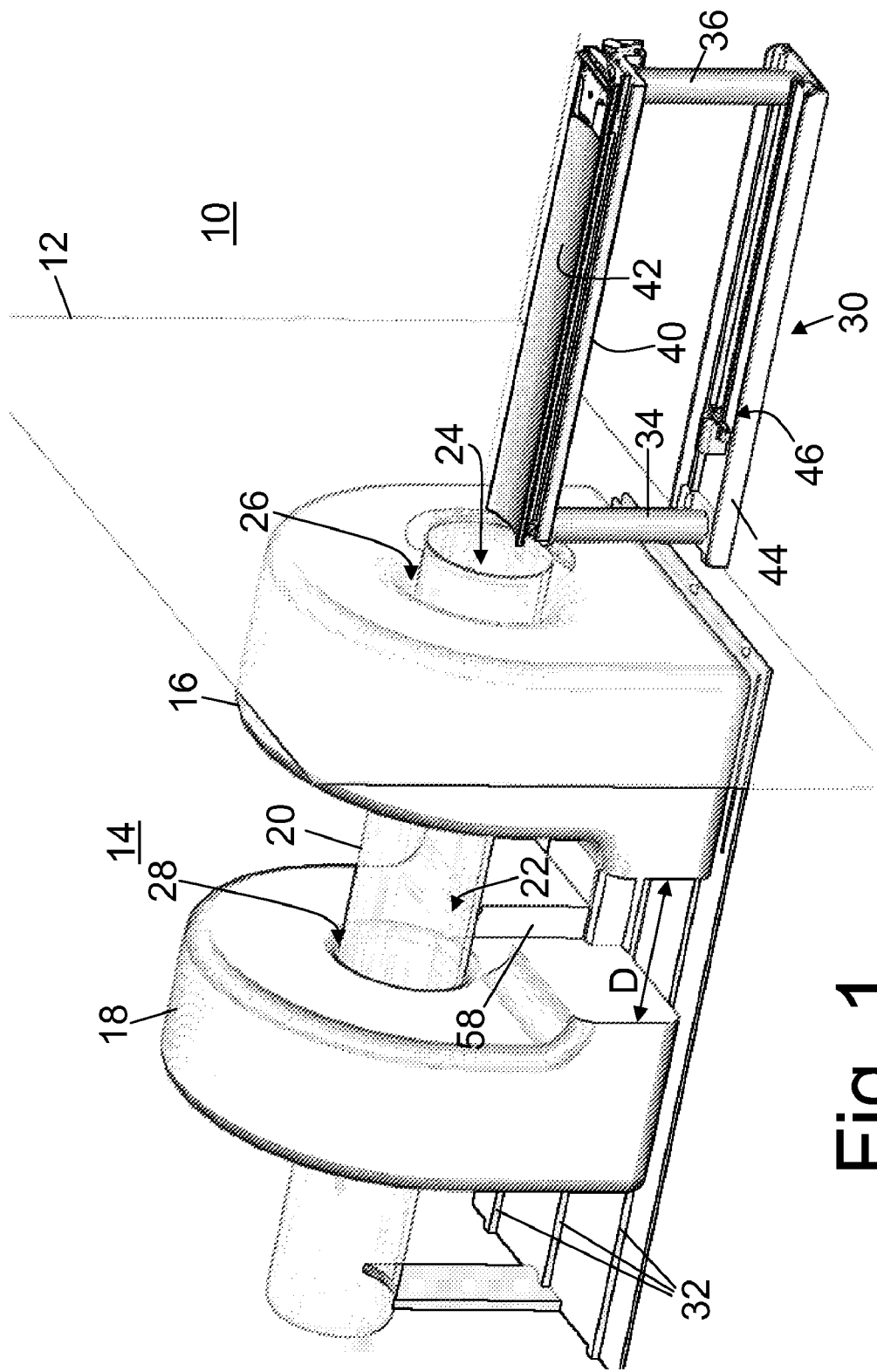

| | | | |
|---|---|---|---|
| 7,382,851 B2 * | 6/2008 | Inoue et al. | 378/4 |
| 7,532,922 B2 * | 5/2009 | Smith et al. | 600/407 |
| 2002/0082496 A1 * | 6/2002 | Kuth | 600/410 |
| 2005/0200360 A1 | 9/2005 | Gewiese | |
| 2008/0171935 A1 * | 7/2008 | McKnight et al. | 5/601 |

OTHER PUBLICATIONS

Ted Shiliksy, "Design Considerations for Placement of Autoclaves in . . . ," Animal LABNews, at http://www.animallab.com/articles.asp?pid=138, pp. 4, 2006.

Raymond Beets, "Cutting-edge BSL-4 labs tough to design, build, operate," R&D Magazine, at http://www.labdesignnews.com/Laboratory Design/LD0509FEAT_1.asp, pp. 4, 2006.

National Institute of Allergy and Infectious Diseases, from Wikipedia, at http://wikipedia.org/wiki/National_Institute_if_Allergy_and_Infectious_Diseases, p. 1, 2006.

Biosafety level, from Wikipedia, at http://en.wikipedia.org/wiki/Biossafety_level, pp. 4, 2006.

National Institute of Allergy and Infectious Deseases Fact Sheet "The Need for Biosafety Laboratory Facilities" http://www.niaid.nih.gov/factsheets/facilityconstruct.

* cited by examiner

SUBJECT TABLE FOR ISOLATION ENVIRONMENT

CROSS REFERENCE TO RELATED APPLICATIONS

This application is a Continuation of PCT/US07/69838 filed May 29, 2007 which claims the benefit of U.S. provisional application Ser. No. 60/804,311 filed Jun. 9, 2006, the subject of which is incorporated herein by reference.

This invention was made with Government support under grant no. N01-A0-60001 awarded by the National Institutes of Health (NIH). The Government has certain rights in this invention.

BACKGROUND

The following relates to the medical imaging and environmental isolation arts, and is described with example reference to medical imaging systems for imaging subjects in contained BioSafety Level 4 (BSL-4) environments. The following finds more general application in medical imaging or other diagnostics performed in conjunction with isolation environments for researching, processing, or otherwise manipulating or containing subjects exposed, or potentially exposed, to radioactive, toxic, biologically infectious, or other hazardous substances. It further finds application in medical imaging in conjunction with performing medical imaging or other diagnostics in isolation environments such as clean rooms, sterile rooms, inert gas environments, and so forth, that are controlled to limit contamination from normal environmental conditions.

Biologically hazardous and highly contagious diseases are an increasing public health concern. Increasing air travel promotes the rapid worldwide spread of contagions. Bioterrorism is another potential route to public exposure to hazardous contagions. Effective response to an outbreak of a contagion is facilitated by knowledge of the infectious agent (that is, the type or species of virus, bacterium, prion, spore, or so forth), effect of counteragents (such as drugs or other types of treatment), transmission pathways (such as airborne transmission, contact transmission, or so forth), incubation period before symptoms arise, and so forth. This knowledge is gained by suitable laboratory studies.

Medical imaging systems, such as magnetic resonance (MR) scanners, transmission computed tomography (CT) scanners, positron emission tomography (PET) scanners, gamma cameras for single-photon emission computed tomography (SPECT), and so forth are powerful tools in detecting physiological manifestations of diseases caused by hazardous contagions, exposure to radioactivity or toxic substances, and so forth. For example, such imaging techniques can detect malignant tumors or other abnormalities that may be indicative of infection or disease. Medical imaging techniques can be applied periodically (for example on an hourly, daily, weekly, or other basis) to image live human or animal subjects so as to track the progression of physiological response to the disease or to exposure to a radioactive or toxic agent. Techniques such as multi-nuclear MR spectroscopy can track metabolic changes associated with the disease progression. These medical imaging-based diagnostics are merely illustrative examples.

Although the benefits of medical imaging systems are well recognized, applying medical imaging systems in the context of an isolation environment has heretofore been difficult. The National Institute of Health (NIH) and Center for Disease Control (CDC) have promulgated operational criteria for laboratories conducting biological research into hazardous contagions. Four levels of isolation have been defined: BioSafety Level 1 (BSL-1), BSL-2, BSL-3, and BSL-4, with the level of isolation increasing with increasing BSL level. The BSL-3 level requires isolation steps such as physical separation of the laboratory working area from access corridors and controlled air flow. BSL-4 requires an isolation zone (sometimes called the "hot zone") with dedicated air flow. The isolation zone is a room, room partition, or building that is sealed off to prevent escape of airborne contagions, and laboratory personnel working within the hot zone wear sealed environmental suits, such as hazardous material (HAZMAT) suits, with self-contained breathing apparatuses. Laboratory personnel and any items that leave the isolation zone must pass through an airlock and undergo specified decontamination procedures before being admitted outside the BSL-4 environment. The isolation environment should be designed to minimize or eliminate sharp corners or features, and to minimize or eliminate fine operational features such as small fasteners, control buttons, or the like which are difficult to manipulate while wearing isolation suit gloves.

The BSL-4 environment is an example. Other isolation environments are used, for example to provide a sterile environment for drug development and testing, to provide isolation of toxic or radioactive materials, or so forth. These isolation environments impose similar constraints such as restricted movement of personnel and equipment, accommodation of limited manual dexterity of gloved or otherwise suited personnel, limiting sharp corners or features, or so forth.

Introducing a complex and sensitive medical imaging instrument such as an MR scanner, CT scanner, or so forth into an isolation environment is problematic. The medical imaging instrument typically includes hundreds, thousands, or more components, some of which are difficult to access to perform decontamination, and some of which may be made of materials that are incompatible with the decontamination procedures applicable in the isolation zone. For example, corrosive chemicals or heating that may be used in BSL-4 decontamination can damage sensitive components of a medical imaging instrument.

Contamination is also problematic for the subject table used to position the subject in the bore or other imaging volume of the medical imaging instrument. Because the infected or potentially infected subject is placed on the subject table, the subject table is frequently decontaminated. For example, in a BSL-4 environment such decontamination should typically include a wipe-down with decontaminant chemicals between subjects, and occasional more extensive decontamination procedures. The subject table should also provide a steady, level surface when inserted into the medical imaging instrument, which imposes mechanical constraints on the table design.

A further consideration is that the subject table is handled or manipulated by personnel working in the isolation environment each time a new subject is loaded into or unloaded from the medical imaging instrument. These personnel may not be radiologists trained in the operation of medical imaging instruments, and may not be skilled in routine table maintenance tasks. Moreover, personnel in isolation environments typically have reduced dexterity due to wearing gloves, HAZMAT suits, or so forth. Contact between the subject table and personnel in the isolation zone can be reduced or even eliminated by automating operations such as translation of the table into and out of the bore or imaging region of the medical imaging instrument, but at the expense of introducing additional mechanical parts which complicate decontamination and may lead to more frequent mechanical failures.

SUMMARY

In accordance with one aspect, a subject loading system is disclosed for moving a subject disposed in an isolation zone into and out of a diagnostic system disposed outside the isolation zone. A tube extends away from the isolation zone. The tube has an inner volume open to the isolation zone and operatively coupled with the diagnostic system. An elongated subject support pallet is disposed in the isolation zone and dimensioned to fit into the tube. A base including a mechanical drive is disposed in the isolation zone and is configured to align the elongated subject support pallet with the tube and to move the elongated subject support pallet into and out of the tube.

In accordance with another aspect, a subject support table is disclosed, including: a subject support pallet; a front support pillar secured to a floor or platform and movably engaged with the subject support pallet; a rear support pillar secured to the subject support pallet and movably engaged with the floor or platform; and a motorized drive disposed on or in the floor or platform and engaging the rear support pillar to move the rear support pillar respective to the front support pillar so as to move the subject support pallet across the front support pillar.

In accordance with another aspect, a subject support table is disclosed for moving a subject into and out of a magnetic resonance (MR) scanner. The subject support table includes: a base; a tabletop disposed at least partially on the base; and a modular motor disposed on or in the base to move the tabletop across the base. The base and the modular motor are configured such that the modular motor is removable only by moving the modular motor in a direction generally away from the MR scanner.

In accordance with another aspect, subject support table is disclosed for use in an isolation zone. An elongated subject support pallet and a base are disposed in the isolation zone. The base is configured to support the elongated subject support pallet. A motorized drive is installed with the base and is configured to move the elongated subject support pallet to extend an end of the elongated subject support pallet toward an associated instrument. The motorized drive includes a modular motor configured to be removably installed with the base as a module.

One advantage resides in providing subject tables that are readily operated by personnel in isolation suits or having otherwise limited dexterity.

Another advantage resides in providing subject tables that are amenable to decontamination using corrosive chemicals.

Another advantage resides in providing subject tables with modular motors in which lubricated or otherwise sensitive motor components are hermetically sealed.

Another advantage resides in spatial separation of intermediate and top pallet motorized drives in multiple-pallet subject tables so as to promote accessibility to the drive components for decontamination and repair.

Another advantage resides in arranging a modular drive motor for an MR scanner table such that the motor is removable only by pulling the modular motor generally away from the magnet of the MR scanner.

Still further advantages of the present invention will be appreciated to those of ordinary skill in the art upon reading and understand the following detailed description.

DRAWINGS

The invention may take form in various components and arrangements of components, and in various steps and arrangements of steps. The drawings are only for purposes of illustrating the preferred embodiments and are not to be construed as limiting the invention.

Figure 2:
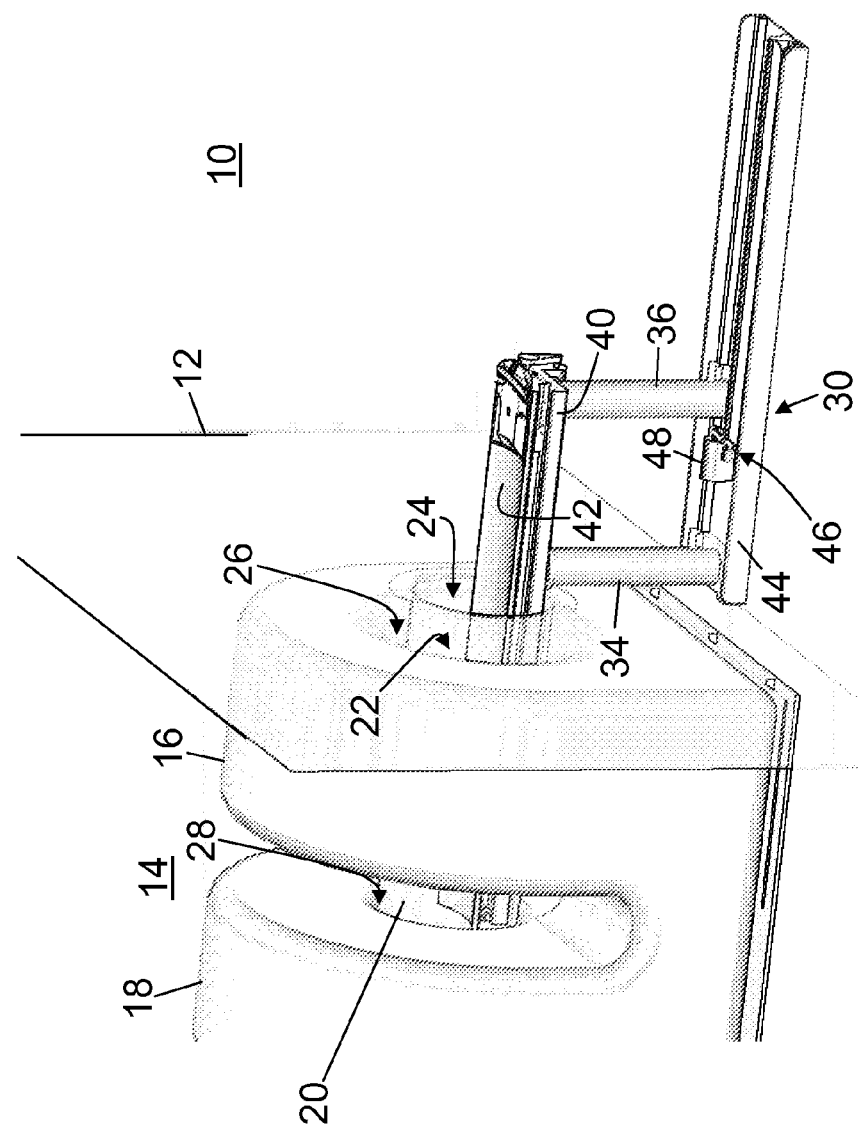

FIGS. 1 and 2 diagrammatically show an isolation zone with combined CT and PET scanners disposed outside and a subject delivery tube extending from the isolation zone into the bores of the CT and PET scanners. FIG. 1 shows the subject pallet retracted, while FIG. 2 shows the subject pallet partially extended into the tube.

Figure 5:
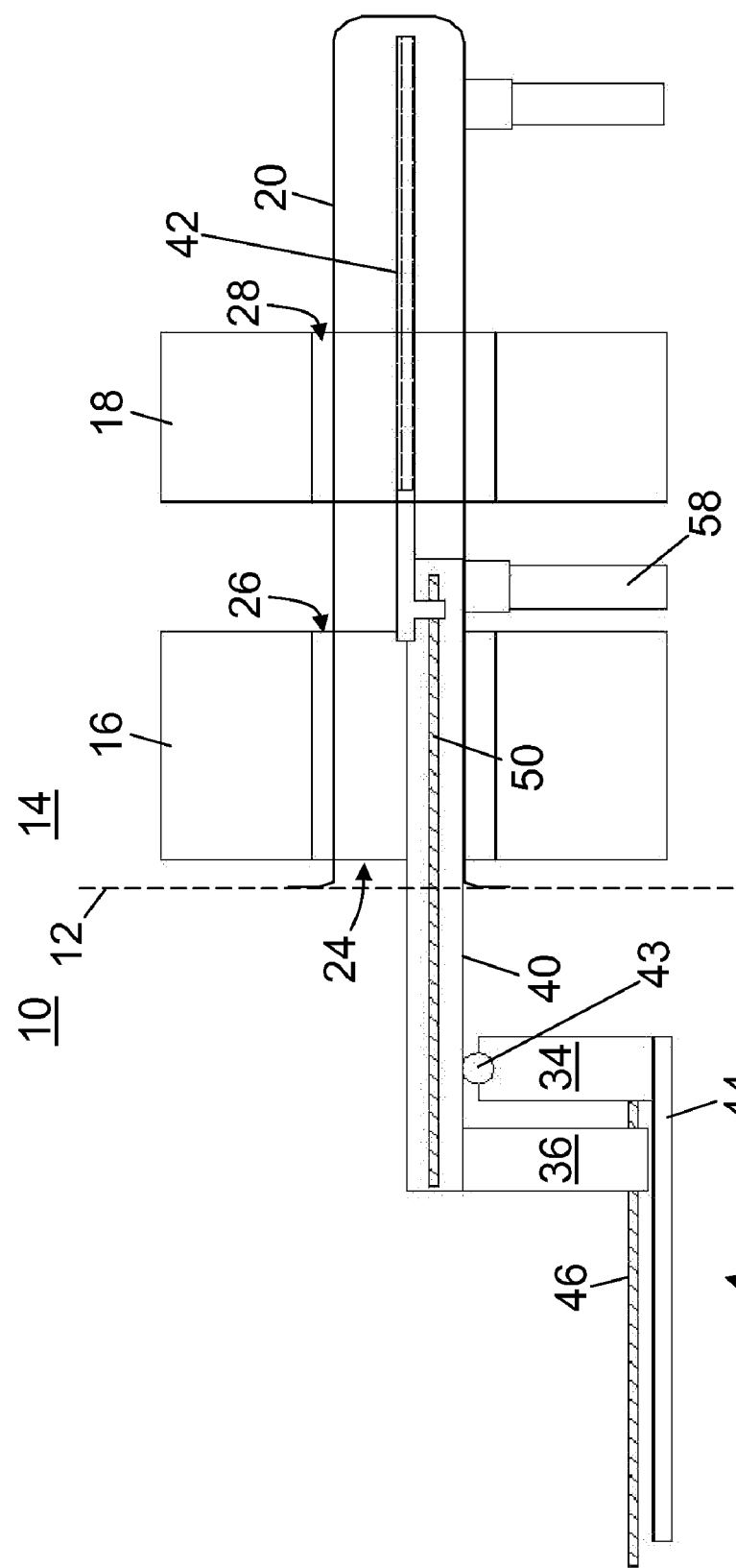
Figure 6:
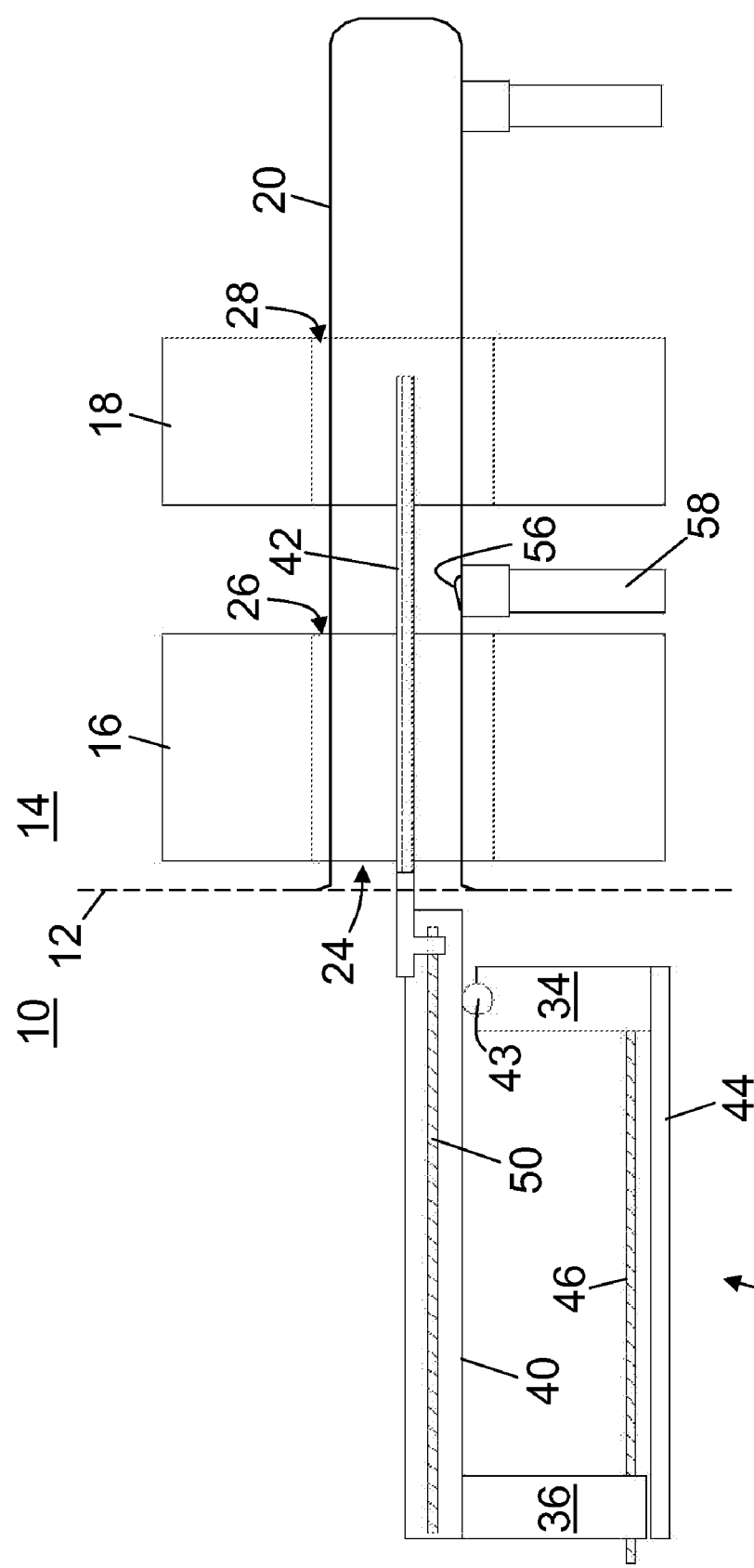
Figure 7:
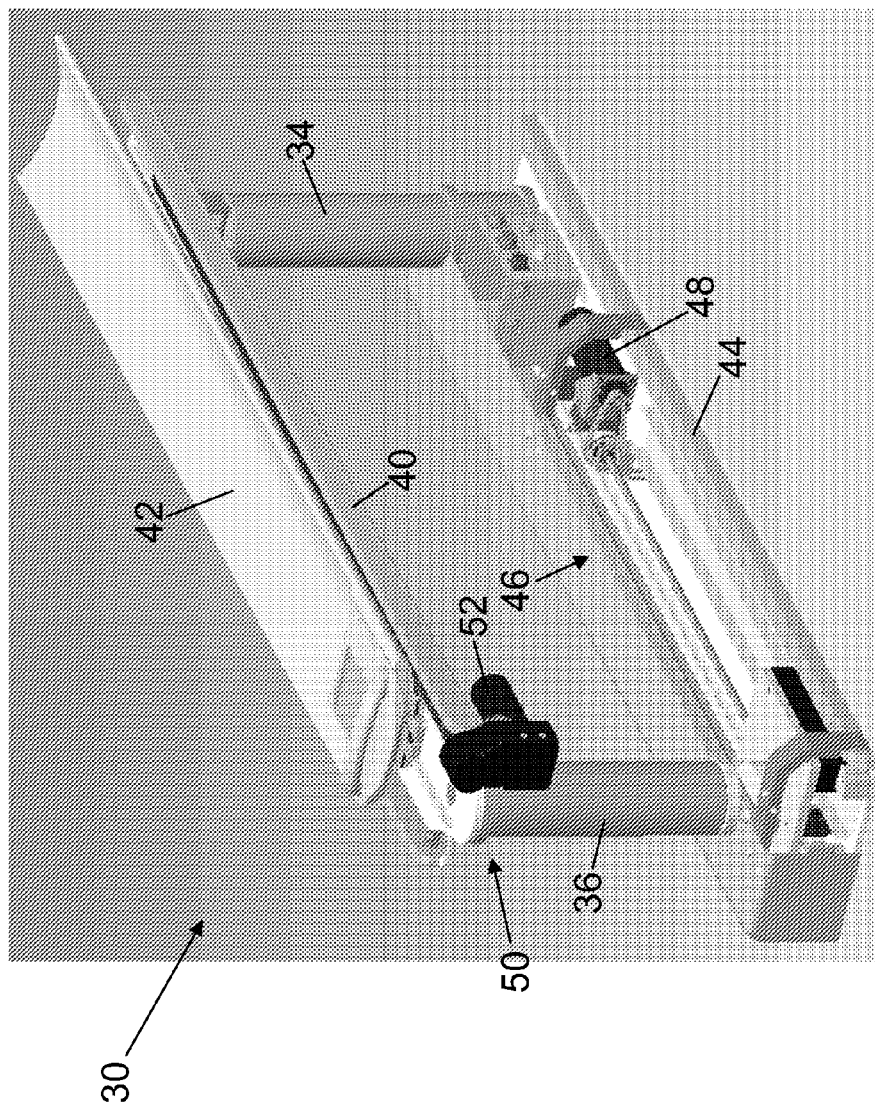
Figure 8:
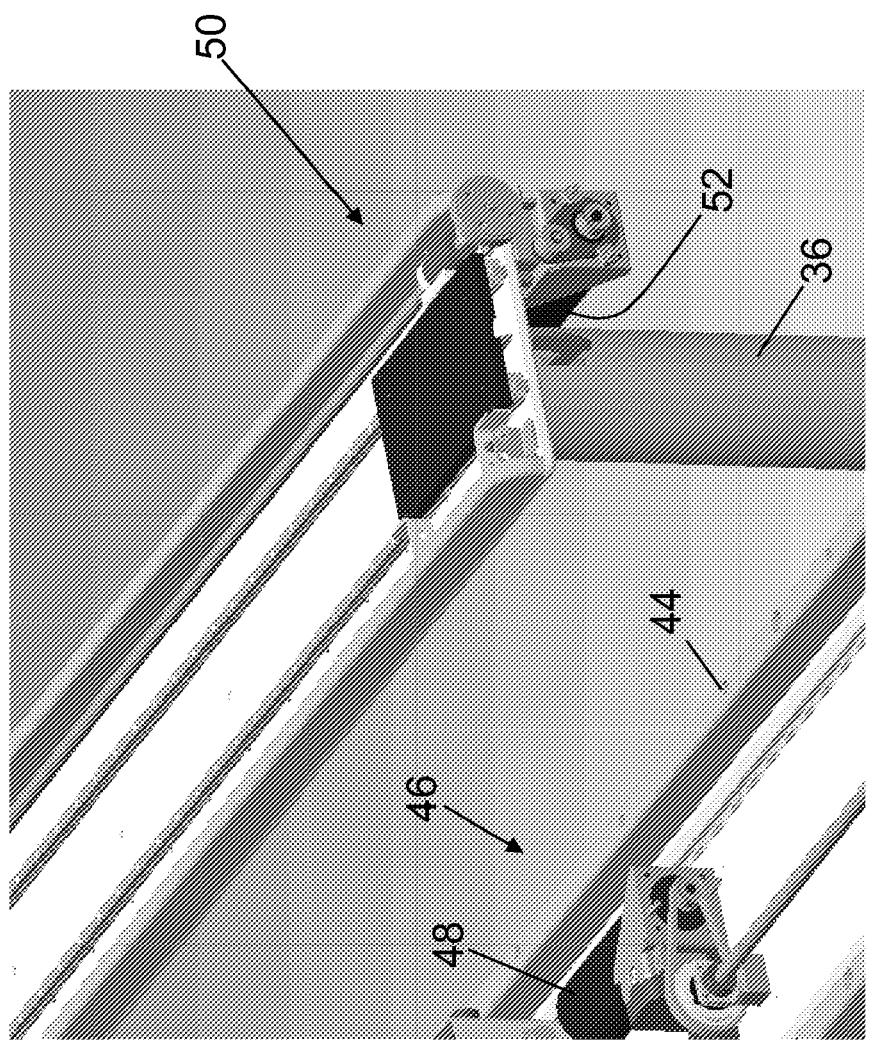
Figure 9:
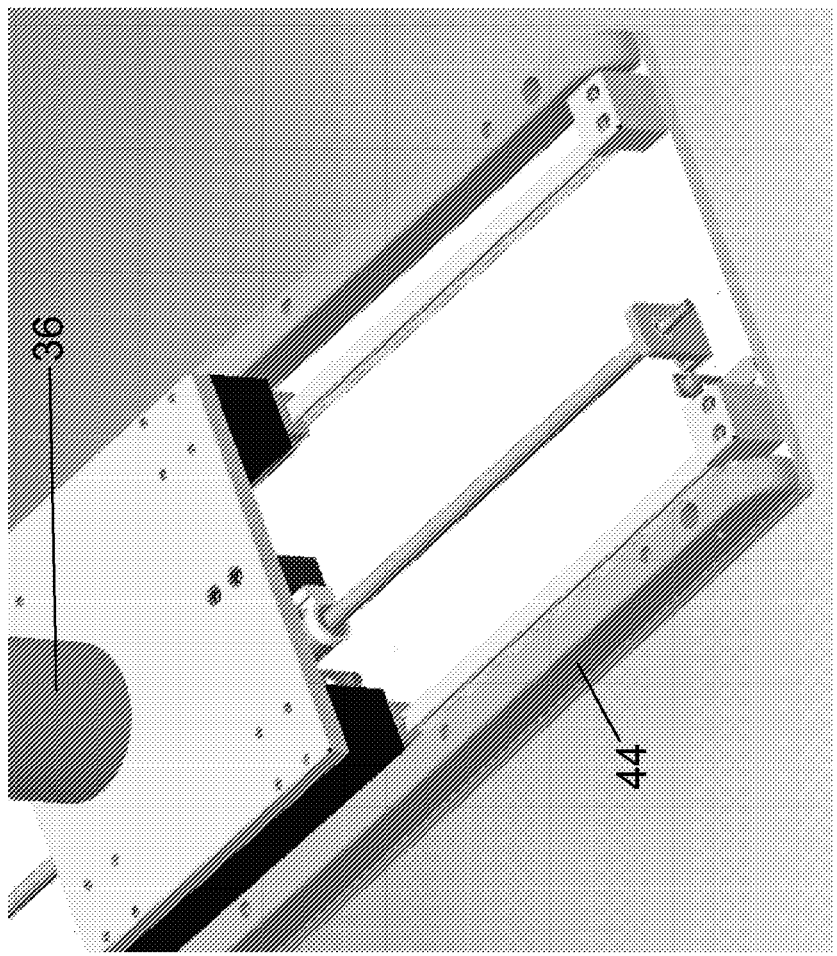
Figure 10:
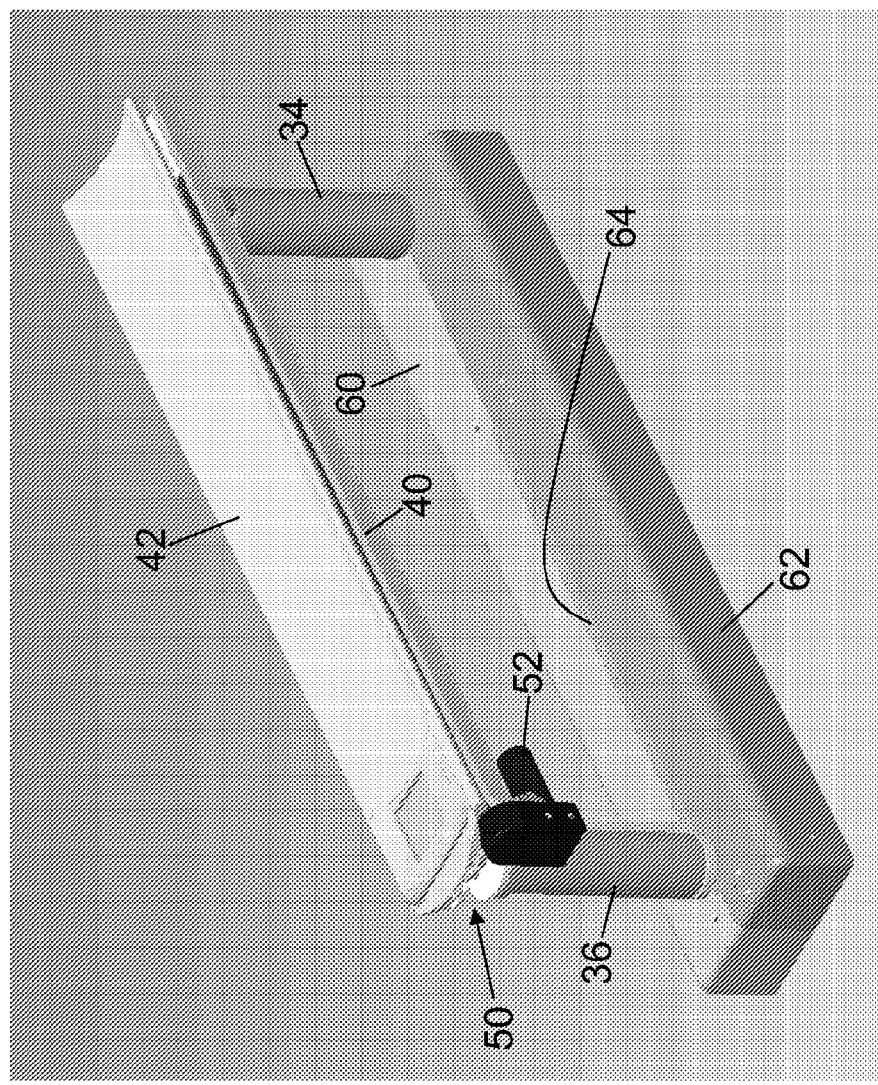

FIGS. 3-10 illustrate the first subject table embodiment for use in conjunction with the CT and PET scanners of FIGS. 1 and 2. FIGS. 3-6 show diagrammatic side views of the isolation zone, the CT and PET scanners, and the first embodiment subject table with the top and intermediate tabletops or pallets in various retracted and extended positions. FIG. 7 shows a perspective view of the first embodiment subject table, with one of the bottom motorized drive covers removed to reveal the bottom drive. FIG. 8 shows a perspective view of a portion of the first embodiment subject table with the top pallet and bottom motorized drive covers removed to reveal the top and bottom motorized drives. FIG. 9 shows a close-up perspective view of the movable engagement of the rear pillar of the first embodiment subject table with the floor or platform in the isolation zone. FIG. 10 shows a perspective view of the first embodiment subject table with the bottom motorized drive covers installed.

Figure 11:
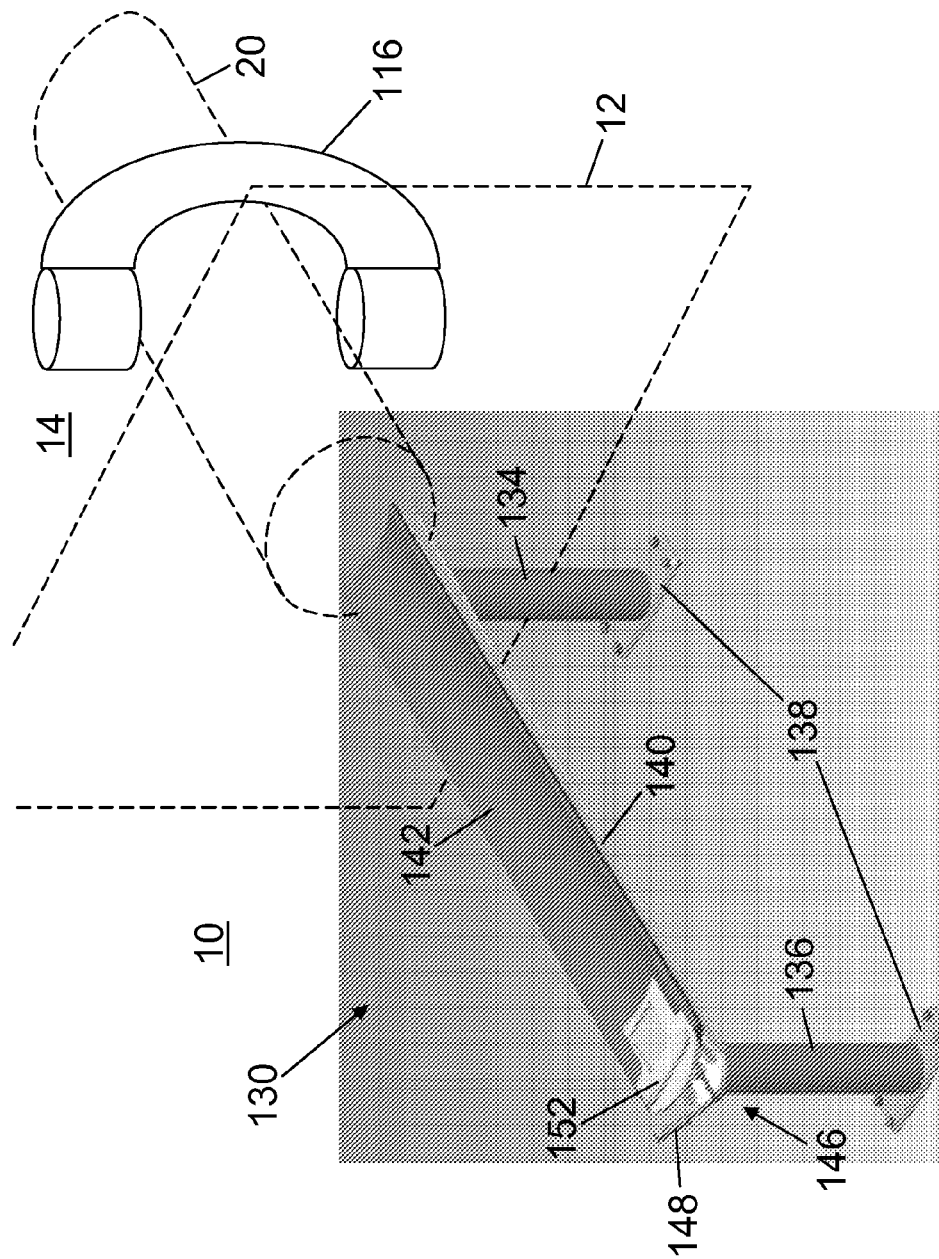
Figure 12:
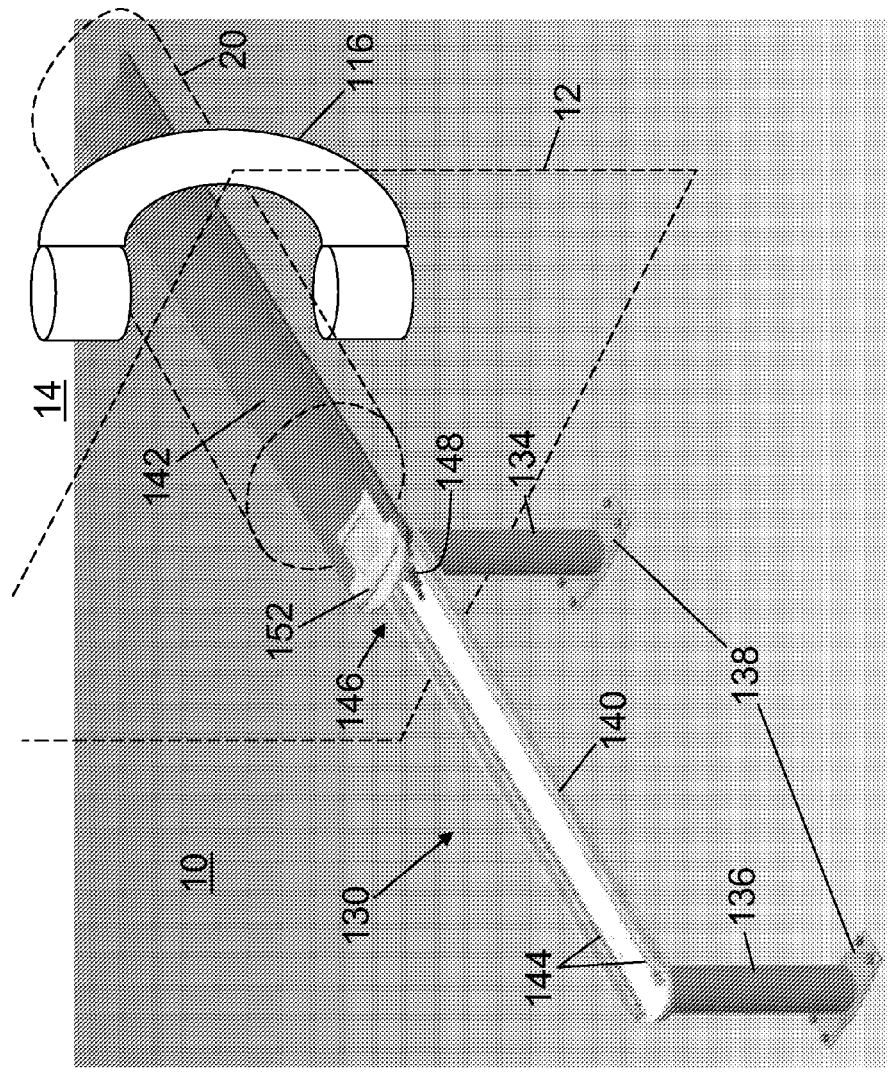
Figure 13:
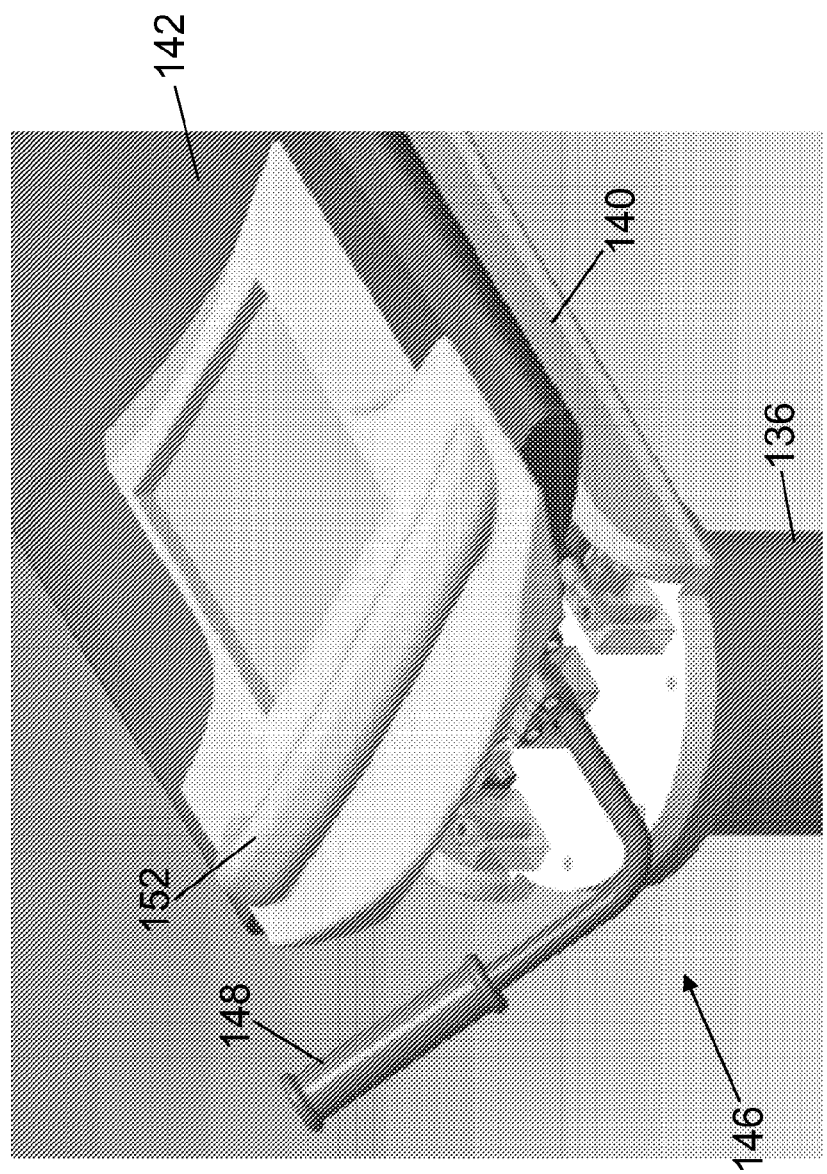
Figure 14:
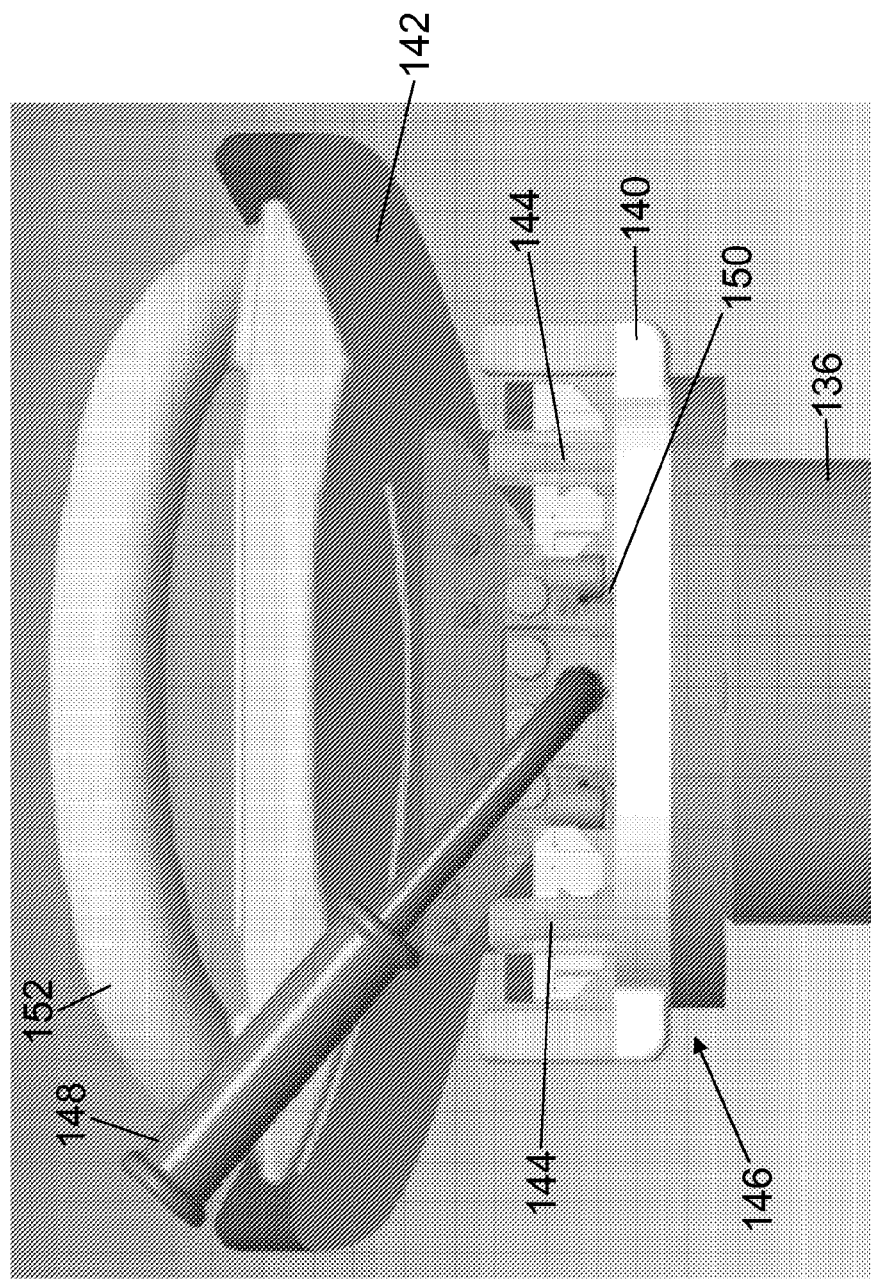
Figure 15:
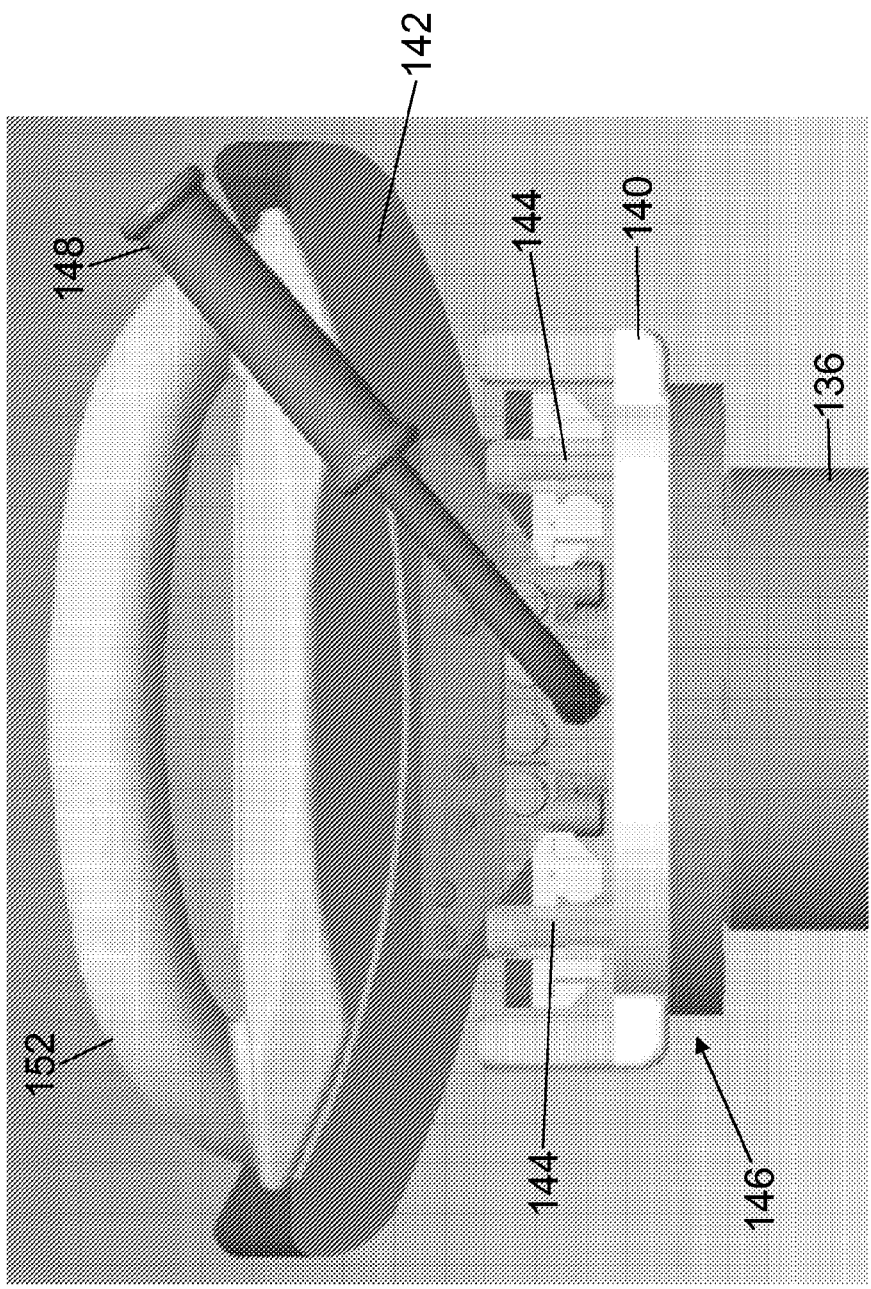
Figure 16:
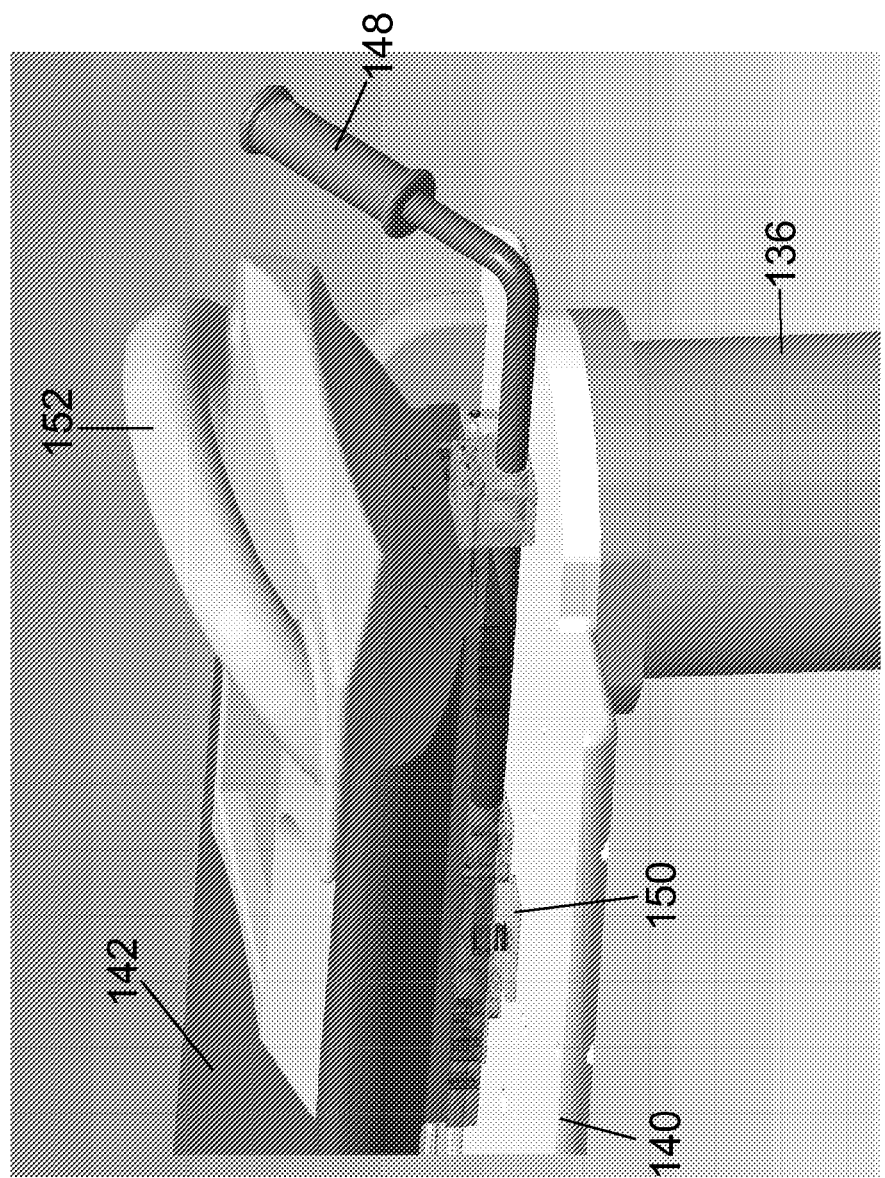

FIGS. 11-16 illustrate a second subject table embodiment, suitable for example for moving subjects into and out of a C-arm x-ray imager. FIGS. 11 and 12 show perspective views of the isolation zone, the C-arm x-ray imager outside the isolation zone, and the second embodiment subject table with the tabletop or pallet retracted and extended into the tube, respectively. FIGS. 13 and 14 show perspective and rear-end views, respectively, of the brake and mechanical drive of the second embodiment subject table with the brake on. FIGS. 15 and 16 show rear-end and perspective views, respectively, of the brake and mechanical drive of the second embodiment subject table with the brake off.

Figure 17:
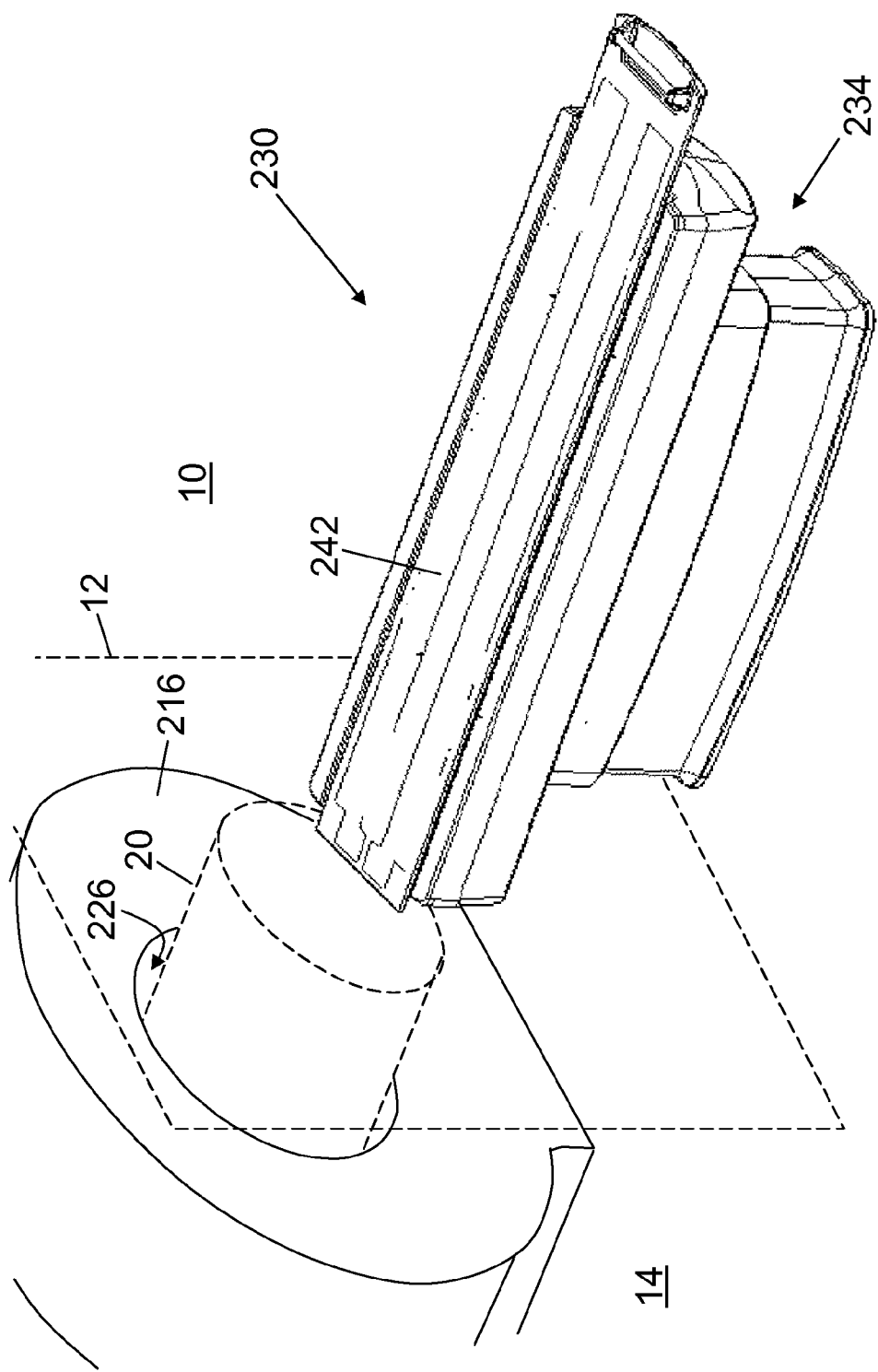
Figure 18:
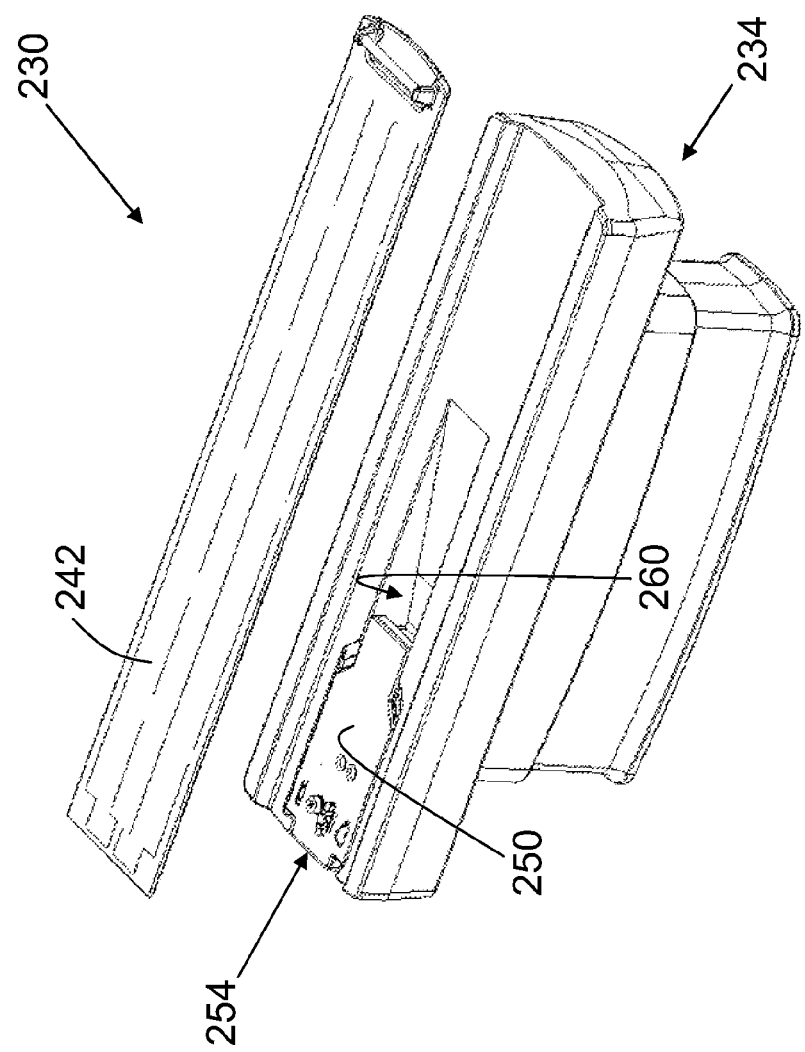
Figure 19:
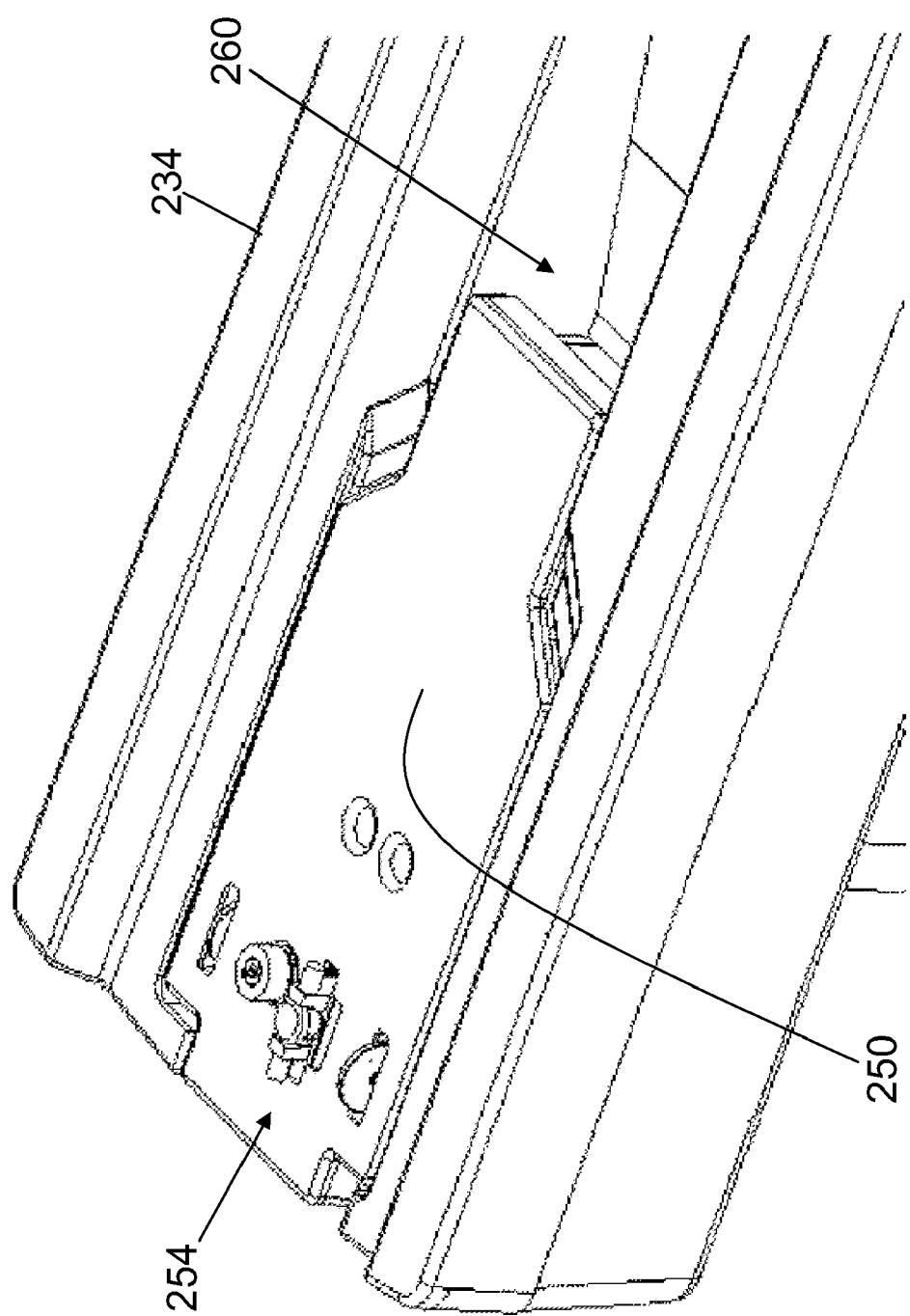
Figure 20:
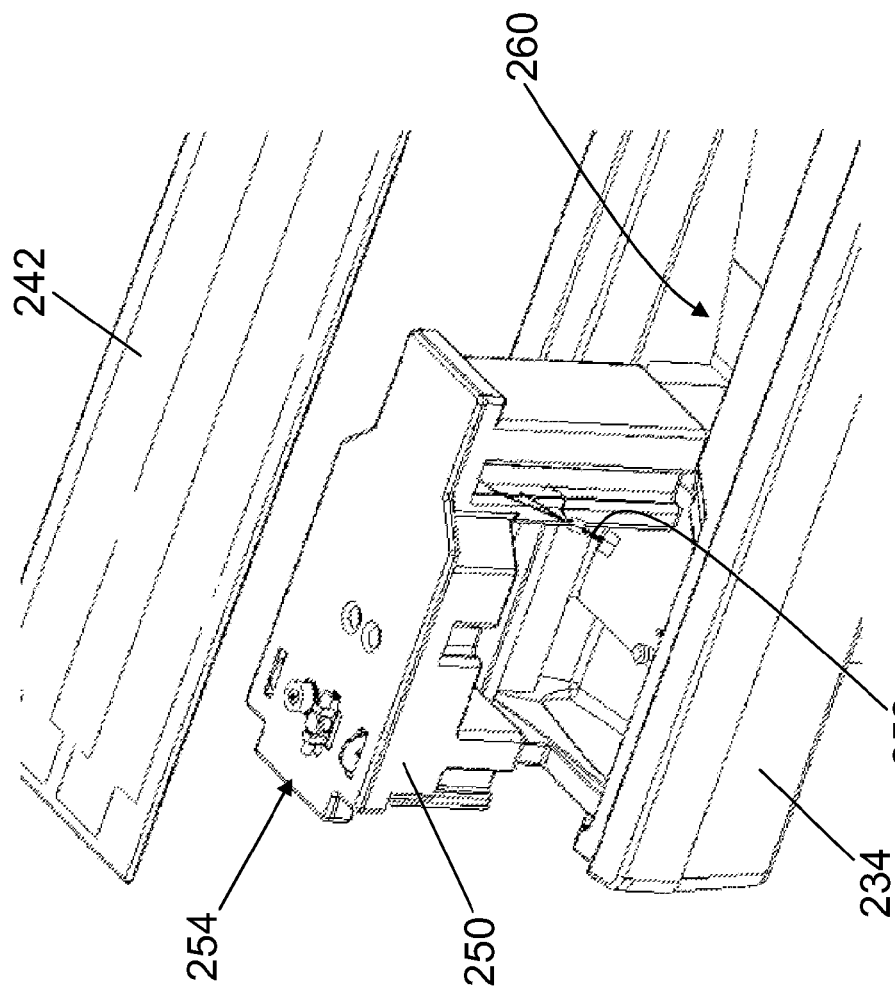
Figure 22:
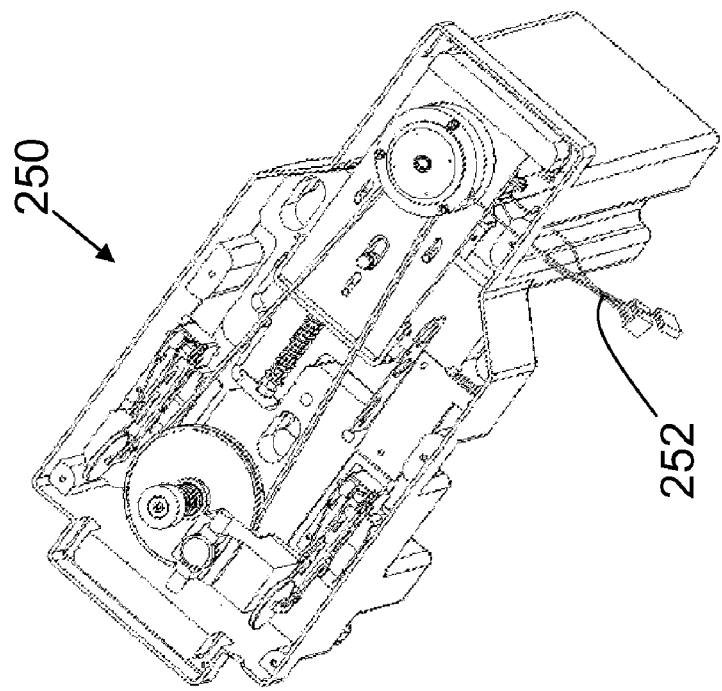
Figure 21:
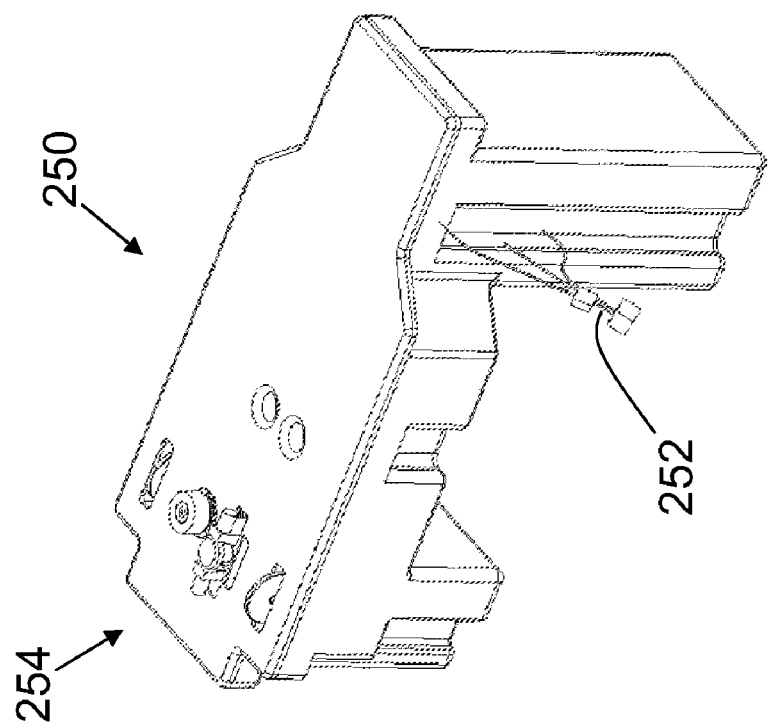
Figure 23:
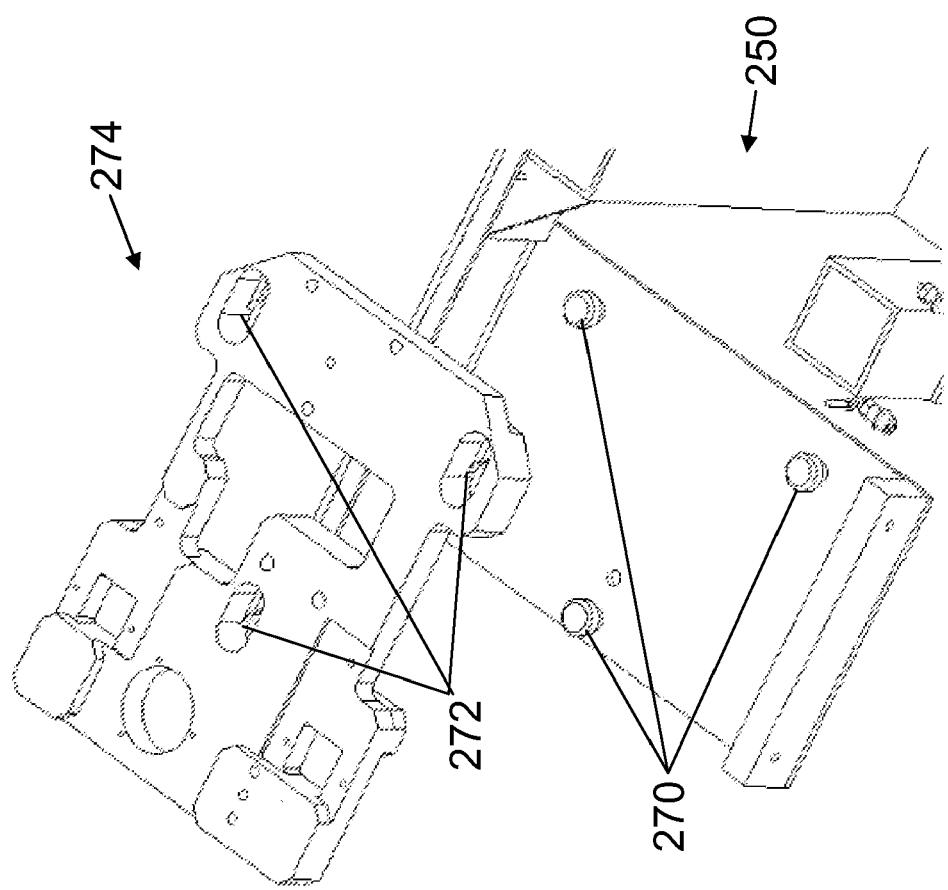
Figure 24:
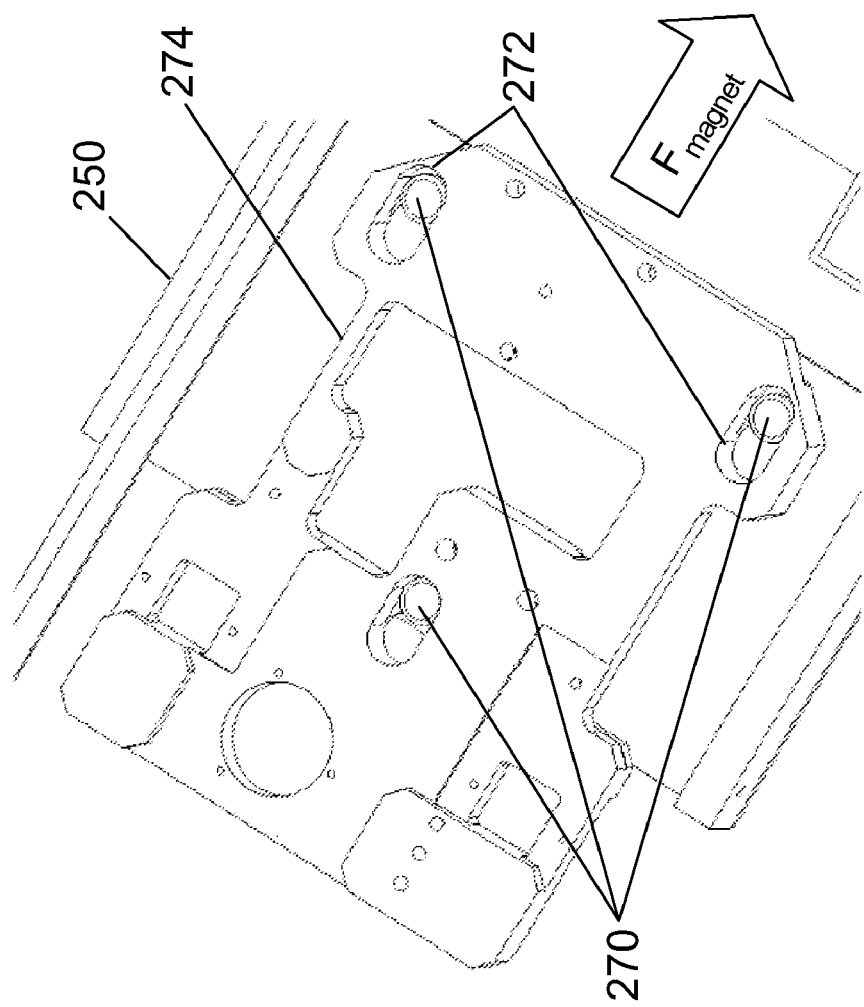
Figure 25:
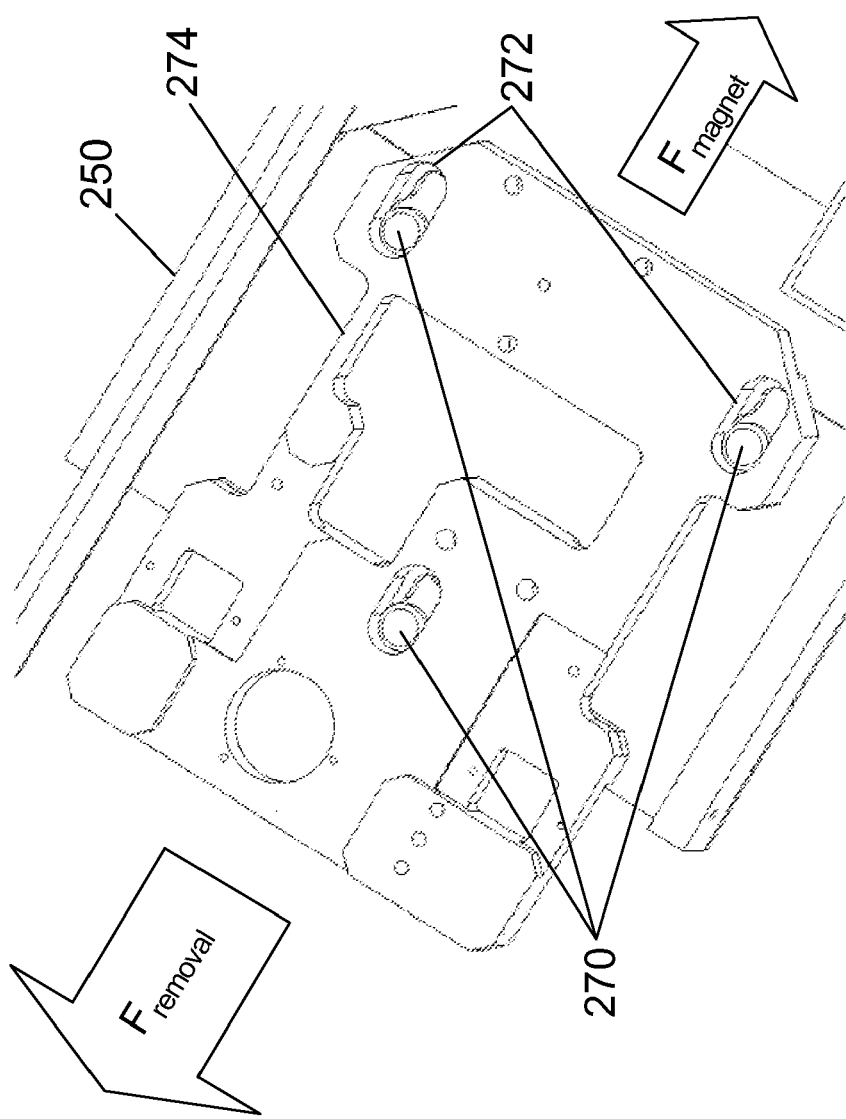

FIGS. 17-25 illustrate a third subject table embodiment, suitable for example for moving subjects into and out of a magnetic resonance (MR) scanner. FIG. 17 shows a perspective view of the isolation zone, the MR scanner outside the isolation zone, and the third embodiment subject table with the tabletop or pallet retracted. FIG. 18 shows a perspective view of the third embodiment subject table with the tabletop or pallet lifted off the base to reveal the mounted modular motor. FIG. 19 shows a close-up of the modular motor mounted in the base. FIG. 20 shows the modular motor removed from the base. FIG. 21 shows the modular motor. FIG. 22 shows the modular motor with a portion of the housing removed to reveal internal components. FIG. 23 is an expanded view of a bayonet-and-keyhole arrangement. FIG. 24 illustrates a locked position. FIG. 25 illustrates an unlocked position.

DESCRIPTION

With reference to FIGS. 1 and 2, an isolation facility includes an isolation zone 10 isolated by a barrier 12 from a less isolated or uncontrolled zone 14. Although a single representative barrier 12 is shown, typically the isolation zone 10 will be enclosed or sealed by a plurality of such barriers, for example by four walls, a floor, and a ceiling defining a sealed room. Access is provided through an airlock door system (not shown). While the representative barrier 12 is shown as a transparent barrier, the barrier may be transparent, translucent, or opaque. For example, in some embodiments the isolation zone 10 is enclosed by stainless steel walls, floor, and ceiling. In some embodiments, the isolation zone 10 is a hot or dirty zone that contains, or may contain, a contagion or infectious agent such as a communicable virus, bacterium, prion, spore, or so forth, or contains or may contain another hazard such as a nerve gas or other toxic chemical, a radioactive material, or so forth. The contagion or toxic or radioactive substance may be communicable by air, by physical contact, by ingestion, by exchange of bodily fluids, or so forth. The contagion or toxic or radioactive substance may actually be present in the air or on surfaces within the isolation zone 10, or may be contained within a glove box, sealed container, or other containment device. In the former case, the isolation zone 10 provides primary containment of the contagion or toxic or radioactive substance; in the latter case, the isolation zone 10 provides a backup or failsafe containment.

In view of the actual or possible presence of the contagion or toxic or radioactive substance in the isolation zone 10, suitable safety standards are employed. In some embodiments, the isolation zone 10 is a biologically hot or dirty zone maintained at BioSafety Level 4 (BSL-4), which entails such precautions as hermetically sealing off the isolation zone 10, keeping the isolation zone 10 at a negative differential pressure respective to the less isolated or uncontrolled zone 14, periodically decontaminating the hot zone 10, limiting access to the isolation zone 10 to qualified personnel wearing sealed environmental suits with self-contained breathing apparatuses, limiting or eliminating sharp objects or corners in the isolation zone 10 (to avoid inadvertent puncturing of the sealed environmental suits), employing a suitable decontamination protocol for personnel or objects leaving the isolation zone 10, and so forth. In other embodiments, the safety standards employed in the isolation zone are selected based on the type of contagion, radioactive substance, toxic substance, or so forth which is present, or potentially present, in the hot zone. In some embodiments, the isolation zone 10 may be a clean room, sterile room, inert gas environment, or other isolation zone that is cleaner or less contaminated than the less isolated or uncontrolled zone 14.

The zone 14 may be a less isolated zone, or may be an uncontrolled zone. For example, if the isolation zone 10 is maintained at BSL-4 isolation, then the zone 14 may be a less isolated zone that is maintained at BSL-3, BSL-2, or BSL-1 isolation or safety level, or the zone 14 may be an uncontrolled zone that is not maintained at any isolation or safety level, and in which personnel and equipment may enter and leave without special precautions.

The isolation facility of FIGS. 1 and 2 includes one or more diagnostic systems, such as illustrated example medical imaging instruments 16, 18, disposed in the less isolated or uncontrolled zone 14. The medical imaging instruments 16, 18 are configured to image a subject, such as a laboratory test animal, an infected person, a contagion transmission vector such as a plant that may carry a contagion, or so forth, disposed on the isolation zone 10. For expository purposes, the medical instruments 16, 18 are considered to be CT and PET scanners, respectively. However, more generally the one or more medical imaging instruments 16, 18 may include, for example, a magnetic resonance (MR) scanner, a positron emission tomography (PET) scanner, a gamma camera for acquiring single-photon emission computed tomography (SPECT) data, a transmission computed tomography (CT) scanner, an x-ray imager, or so forth. Still more generally, the diagnostic systems 16, 18 may include one or more non-imaging diagnostic systems such as an optical or magnetic resonance spectroscopy system, a Geiger counter, or so forth (not illustrated). Medical imaging instruments or other diagnostic systems are typically expensive and typically include a large number of parts, some of which may be incompatible with corrosive substances, heating, or other decontamination procedures employed in the isolation zone 10.

Accordingly, the diagnostic systems 16, 18 are disposed in the less isolated or uncontrolled zone 14 and image or otherwise operatively couple with the subject disposed in the isolation zone 10 through a suitable tube 20 arranged at the barrier 12 extending away from the isolation zone 10. The tube 20 has an inner volume 22 open to the isolation zone 10 and operatively coupled with the diagnostic systems 16, 18. An opening 24 of the tube 20 communicates with the isolation zone 10. The interior volume 22 of the tube 20 is isolated from the less isolated or uncontrolled zone 14, for example by having the edges of the opening 24 hermetically sealed with the barrier 12 and having a sealed cap or other closure at is far end, which closure may be made of the same material, and is optionally contiguous with, the tube. In other embodiments, the cap may be of a different material from that of the tube. In the illustrated embodiment, the tube 20 is cylindrical with a circular cross-section, and passes through a bore 24 of the first medical imaging instrument 16 and through a bore 26 of the second medical imaging instrument 18. It will be appreciated that the illustrated tube 20 is an example—in other contemplated embodiments, the tube may have a conical shape with a taper, may have an elliptical, rectangular, square, or otherwise-shaped cross-section, or so forth.

The tube 20 allows for the subject in the isolation zone 10 to be operatively coupled with the diagnostic system or systems 16, 18 disposed outside the isolation zone 10. For example, if the diagnostic system or systems 16, 18 are medical imaging systems, then the tube 20 allows for imaging of a subject disposed in the interior 22 of the tube 20. Depending upon the imaging or diagnostic modality, the tube 20 may or may not be optically transparent. For example, in the case of an MR scanner, the tube 20 can be optically opaque or optically transparent, but should be non-magnetic to enable the radio frequency fields and applied magnetic fields and magnetic field gradients to pass through the tube 20 substantially unimpeded. For computed tomography imaging, the tube 20 should be made of a material that is substantially transparent to the transmitted x-rays. For PET or SPECT imaging, the tube 20 should be made of a material that is substantially transparent to the radiation emitted by a radiopharmaceutical that is administered to the subject. For example, in PET imaging, 511 keV gamma rays emitted by positron-electron annihilation events should pass substantially unattenuated through the tube 20. For photographic imaging, the tube 20 should be optically transparent. For diagnostic monitoring using a Geiger counter, the tube should be substantially transparent to the type of radiation that may be present in the subject.

Advantageously, the diagnostic systems 16, 18 are disposed outside of the isolation zone 10, and hence do not undergo decontamination or other biological safety procedures that are applicable to personnel and items disposed in the isolation zone 10. The diagnostic systems 16, 18 can, for example, be operated by personnel located in the less isolated or uncontrolled zone 14 who are not wearing sealed environmental suits. However, a subject table 30 used to move a subject into and out of the interior volume 22 of the tube 20 is disposed inside the isolation zone 10.

In FIG. 1 the second medical imaging instrument 18 moved away from the first medical imaging instrument 16 by a distance D. In the illustrated embodiment, there is a movable engagement 32, such as illustrated rails 32, between the imaging instrument 18 and a platform or floor supporting the imaging instrument 18 outside the isolation zone 10. The movable engagement enables the imaging system 18 to be linearly moved along the tube 20 between an operative position (shown in FIG. 2) and a maintenance position (shown in FIG. 1). In the maintenance position of FIG. 1, the second medical imaging instrument 18 is separated from the first medical imaging instrument 16 so as to facilitate repairs or maintenance of the medical imaging instruments 16, 18. For example, if the medical imaging instrument 16 is a CT scanner, separating the medical imaging instruments 16, 18 by the distance D may facilitate removal of a gantry housing panel of the CT scanner to access the x-ray tube (not shown) for replacement. It is to be appreciated that the maintenance and operative positions may be discrete positions, or may be approximate positions or position ranges. For example, the maintenance position may be a continuous range of positions or values for the distance D which are sufficiently large to facilitate the intended maintenance activity.

With continuing reference to FIGS. 1 and 2, and with further reference to FIGS. 3-10, the subject table 30 includes a base that includes a front support pillar 34 and a rear support pillar 36. A pallet assembly includes an intermediate elongated tabletop or pallet 40 and a top elongated tabletop or pallet 42. The front support pillar 34 is secured to a floor or platform 44 and is movably engaged with the intermediate elongated pallet 40. For example, the intermediate elongated pallet 40 may slide across the front pillar 34, or may roll on rollers 43 disposed between the intermediate elongated pallet 40 and the top of the front pillar 34, or so forth. The rear support pillar 36 is secured to the intermediate elongated pallet 40 and is movably engaged with the floor or platform 44. A bottom motorized drive 46 including a modular motor 48 is disposed on or in the floor or platform 44 and engages the rear support pillar 36 to move the rear support pillar 36 respective to the front support pillar 34 so as to move the intermediate elongated pallet 40 and the top elongated pallet 42 together across the front support pillar 34 and into or out of the tube 20. Additionally, a top motorized drive 50 including a modular motor 52 is disposed on or in the intermediate elongated pallet 40 and engages the top elongated pallet 42 to move the top elongated pallet 42 respective to the intermediate elongated pallet 40.

The motorized drives 46, 50 are spatially separated, with the motorized drive 46 for the intermediate elongated pallet 40 disposed on or in the floor or platform 44 and the motorized drive 50 for the top elongated pallet 42 disposed on or in the intermediate elongated pallet 40. Such spatial separation of the drives promotes accessibility for decontamination or repair of the drive components. Additionally, locating the motorized drive 46 for the intermediate elongated pallet 40 on the floor reduces the weight supported by the pillars 34, 36 and enables the intermediate elongated pallet 40 to be less heavy and more compact. These are advantages in the context of the isolation environment of FIGS. 1 and 2, but are also advantages in other settings including conventional hospital or other medical facility settings.

Figure 3:
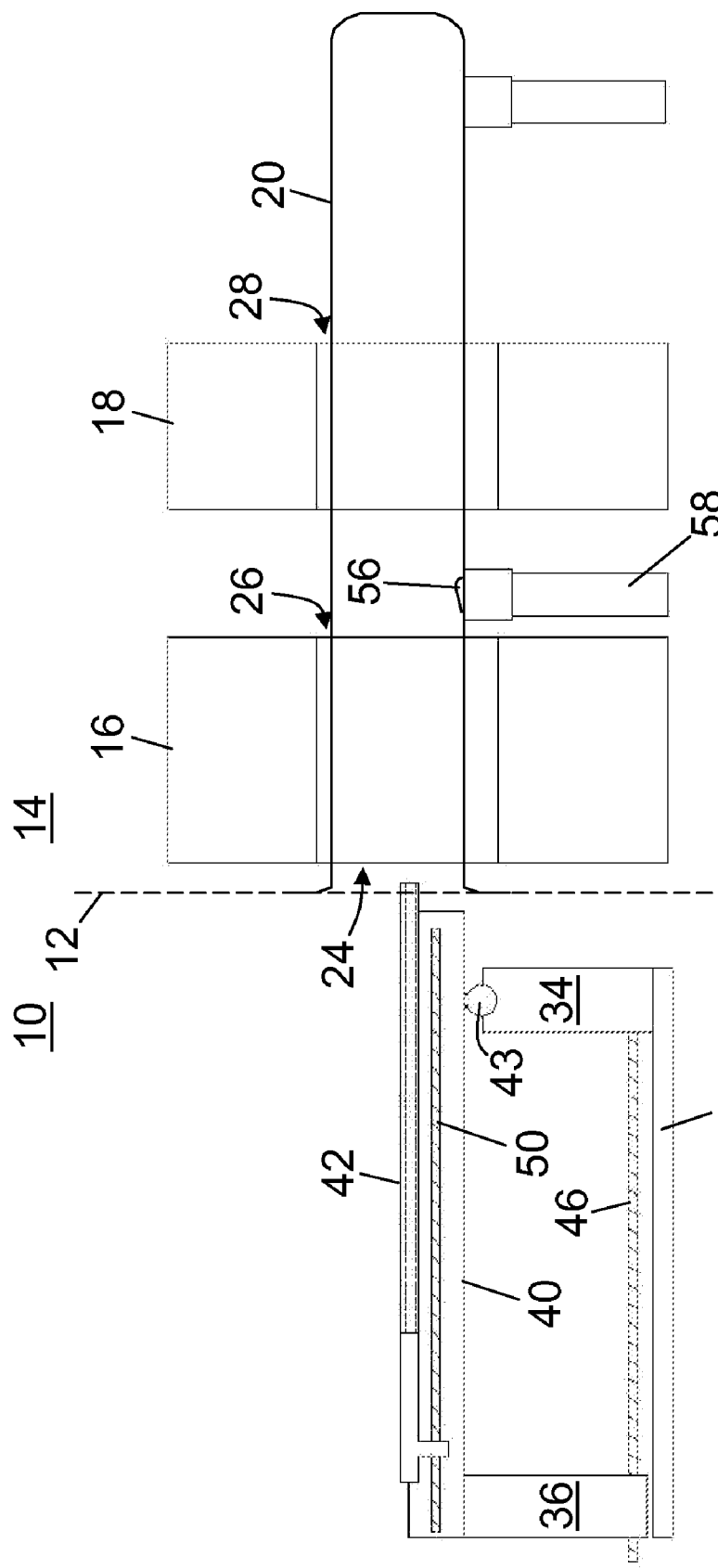

FIG. 3 shows the subject table 30 with both pallets 40, 42 fully retracted. FIG. 3 also shows an engagement element 56, such as a ramp 56, disposed in the tube 20 to engage and stop forward insertion of the elongated intermediate pallet 40 into the tube 20. In the illustrated arrangement, the engagement element 56 is aligned with a tube support 58 disposed outside the isolation zone 10 and supporting the tube 20, such that the tube 20 supports the engagement element 56 at the position of the tube support 58 to reduce deflection of the otherwise cantilevered pallet 40.

Figure 4:
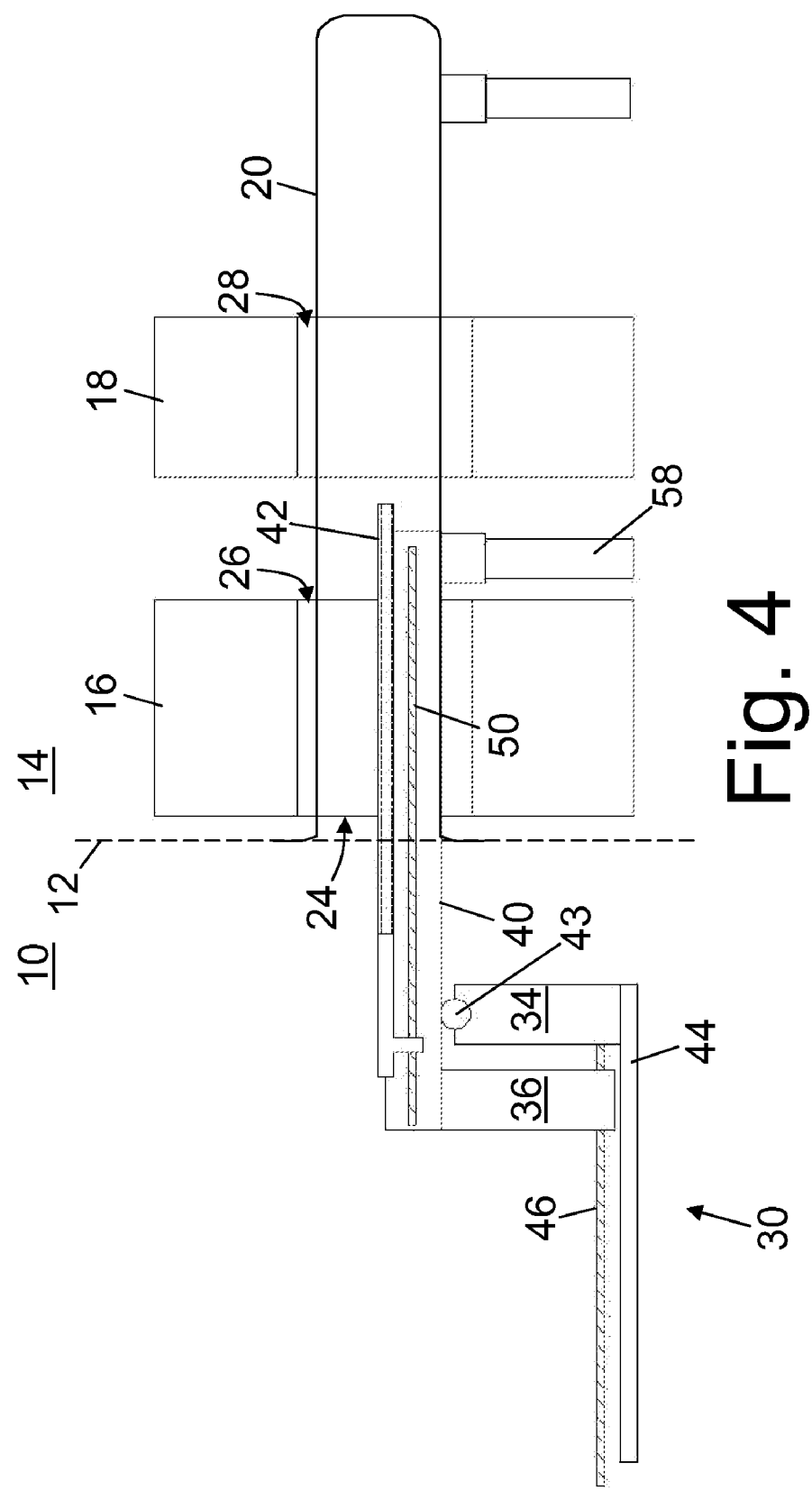

FIG. 4 shows extension of the intermediate elongated pallet 40 using the bottom motorized drive 46, while FIG. 5 shows an additional extension of the top elongated pallet 42 using the top motorized drive 50 (see FIG. 5). As shown in FIG. 4, intermediate elongated pallet 40 extends to engage with the engagement element 56, which provides support for the intermediate elongated pallet 40 in its extended position. Because the engagement element 56 is aligned with the tube support 58, the stress on the tube 20 is limited. In embodiments in which the tube 20 is made of a sufficiently strong and rigid material, however, it is contemplated to arrange the engagement element in the tube in a position not aligned with a tube support. As shown in FIG. 5, when the top elongated pallet 42 is also extended, it is positioned in the bore 28 of the second medical imaging instrument 18 (which may, for example, be a PET scanner), and is supported in cantilevered fashion from the intermediate elongated pallet 40.

Optionally, the bottom motorized mechanical drive 46 is interlocked such that the elongated intermediate pallet 40 cannot be moved out of the tube 20 unless the elongated top pallet 42 is in a retracted position. The interlock avoids unbalanced table configurations in which the elongated intermediate pallet 40 is partially retracted and hence unsupported by the engagement element 56 while the top pallet 42 is extended to produce substantial torque on the intermediate pallet 40.

With reference to FIG. 6, to perform imaging using the first medical imaging instrument 16 arranged closest to the isolation zone 10 (which may, for example, be a CT scanner), starting from the fully retracted position of FIG. 3 the intermediate elongated pallet 40 remains retracted, and the top elongated pallet 42 is extended using the top motorized drive 50 to move the top elongated pallet 42 into the tube 20 aligned with the bore 26 of the first medical imaging instrument 16. In this arrangement, the top elongated pallet 42 is supported in cantilevered fashion from the base including the retracted intermediate pallet 40.

To use the subject table 30 in a BSL-4 or other high-level isolation environment, provisions are suitably made to support decontamination procedures. For example, as shown in FIG. 10, the bottom motorized drive 48 is optionally covered by covers 60, 62. A rubber strip seal 64 arranged between the covers 60, 62 substantially seals a slot in the drive covers 60, 62 along which the rear support pillar 36 is movably engaged. The pillar 36 is suitably narrowed to a "T"-shape at the bottom to enable sealing with the narrow strip seal 64. In this fashion, the bottom motorized drive 48 is substantially sealed against inadvertent liquid ingress or objects falling into the bottom motorized drive 48. In some embodiments, the modular motors 48, 52 of the bottom and top motorized 46, 50, respectively, are interchangeable, so that a single type of modular motor can be stored in the isolation zone 10 to enable swapping out a modular motor for decontamination or to address a motor malfunction. The modular motors 48, 52 are optionally also hermetically sealed so that only the outside of the motor is exposed to the environment of the isolation zone 10. In some embodiments, the top elongated pallet 42 is configured to be easily removable to facilitate decontamination of the underlying top motorized drive 50.

Components of the subject table 30 are suitably made of stainless steel which is compatible with typical decontamination chemicals and processes such as those employed in BSL-4 isolation. Screws are suitably Teflon-coated to provide resistance to decontamination chemicals and processes, and to reduce the likelihood that a screw will seize. Through holes, counter bores, and the like are suitably filled with epoxy, silicone, or so forth to reduce points for collection of contamination. The translating electrical cables for the motorized drives 48, 50 are suitably ribbon cables, which are easy to wipe down during routine decontamination. The motorized drives 48, 50 are optionally configured for easy removal to promote decontamination or replacement. For example, in one embodiment Teflon-coated screws at opposite ends of the drive assembly are removed in order to lift off a motorized drive. The front and rear pillars 34, 36 are suitably hollow stainless steel cylinders. The ends of the front pillar 34 are suitably welded closed to seal the interior of the steel cylinder, so that only the outside of the front pillar 34 is exposed to the isolation zone 10. The ends of the rear pillar 36 are suitably sealed with rubber boots to prevent ingress of contaminants. Electrical cables are optionally located outside of the pillars 34, 36 to promote easy replacement and decontamination of the cables.

The subject support 30 is an illustrative example, suitably adapted to enable positioning a subject disposed on the top elongated pallet 42 in either the bore 26 of the medical imaging instrument 16, or in the bore 28 of the medical imaging instrument 18.

With reference to FIGS. 11-16, another subject table 130 is described, which is suitable, for example, for positioning a subject in a diagrammatically illustrated C-arm x-ray imager 116 disposed in the less isolated or uncontrolled zone 14. The subject table 130 is disposed in the isolation zone 10, and includes front and rear support pillars 134, 136, both of which are secured to the floor or platform of the isolation zone 10, for example via the illustrated base plates 138. The opposite ends of the support pillars 134, 136 are secured to an elongated horizontal base member 140. An elongated tabletop or pallet 142 is supported by the elongated horizontal base member 140, and is dimensioned to fit inside the tube 20 (shown in phantom in FIGS. 11 and 12). In the retracted position (FIG. 11), the pallet 142 lies substantially on top of the base member 140. In the extended position (FIG. 12), the pallet 142 is moved along rails 144 of the base member 140 into the tube 20. The portion of the pallet 142 that extends off the horizontal base member 140 is supported in cantilevered fashion by the base member 140 as it extends into the tube 20 to coincide with an imaging region of the C-arm x-ray imager 116. Because the subject table 130 includes a single pallet component 142 rather than two pallet components 40, 42 as in the subject table 30, the subject table 130 suited for imaging tasks which involves limited or short-distance translation of the subject, such as a single imaging system in which the subject is not translated during imaging. However, the subject table 130 is also contemplated for other uses, such as helical CT imaging in which the subject is translated during imaging.

Unlike the motorized subject table 30, the subject table 130 of FIGS. 11-16 includes a manual mechanical drive 146 best seen in FIGS. 13-16. To facilitate operation by personnel wearing gloves or other dexterity-limiting isolation apparel, the mechanical drive 146 is designed to involve only manual pushing or pulling of the pallet 142, and manipulation of a hand brake 148. FIGS. 13 and 14 show the hand brake 148 in the "on" (that is, braked) position, in which the lever of the hand brake 148 presses a frictional brake element 150 between the pallet 142 and the horizontal base member 140 to produce frictional braking. The frictional brake element 150 frictionally locks the pallet 142 respective to the base member 140 to prevent the pallet 142 from being moved respective to the base member 140 when the brake 148 is on. FIGS. 15 and 16 show the configuration with the hand brake in the "off" (that is, unbraked) position which withdraws the frictional brake element 150 to allow the pallet 142 to be moved respective to the elongated horizontal base member 140. The movement of the pallet 142 is suitably performed manually by pushing or pulling on a suitable handhold such as the hand brake 148 or a pallet handle 152.

With reference to FIGS. 17-25, another subject table 230 is described, which is suitable, for example, for positioning a subject in a diagrammatically illustrated magnetic resonance (MR) scanner 216 disposed in the less isolated or uncontrolled zone 14 with the tube 20 passing through a scanner bore 226 of the MR scanner 216. In other embodiments, the MR scanner may be an open bore scanner or have some other imaging region configuration. The subject table 230 includes a base 234 disposed on a floor or platform in the isolation zone 10, and a tabletop or pallet 242 supported by the base 234. A modular motor 250 disposed in the base 234 is geared to move the tabletop or pallet 242 along a generally horizontal top surface of the base 234 and into the tube 20. In some embodiments, the tube 20 is supported by the walls of the scanner bore 226 so that the tube 20 can support substantial weight—in such embodiments, the tabletop or pallet 242 may be supported by the lower tube wall as it moves into the tube 20. In other embodiments, it is contemplated to have the tabletop 242 supported in cantilevered fashion from the end of the base 234 as it moves into the tube 20, similarly for example to the cantilevered arrangement of the pallet 142 of the subject table 130 of FIGS. 11-16.

As shown in FIG. 18, to facilitate decontamination and access to underlying components, the tabletop or pallet 242 is removable from the base 234, so as to expose the modular motor 250. As shown in FIG. 20, with the tabletop 242 removed the modular motor 250 can be removed as a unit from the base 234. As shown in FIGS. 21 and 22, the modular motor 250 is a hermetically sealed unit that contains the lubricated elements of the motorized tabletop drive (see FIG. 22, where the top cover of the sealed housing of the motor 250 is removed to reveal internal components). Accordingly, the modular motor 250 can be removed as a unit and bagged for decontamination, and replaced by another modular motor. The modular motor 250 includes an electrical cable 252 that is configured to connect with an electrical panel (not shown) in the isolation zone 10. The modular motor 250 also includes exposed mechanical gearing 254 that operatively connects with corresponding mechanical gearing (not shown) on the underside of the tabletop or pallet 242.

The modular motor 250 is in relatively close proximity to the MR scanner 216. Accordingly, the MR scanner 216 produces an attractive magnetic field which may attract the modular motor 250 toward the tube 20 and the bore 226. To minimize the risk that the modular motor 250 will be inadvertently drawn toward the MR scanner 216 during removal by the magnetic force, the mounting of the modular motor 250 in the base 234 is configured such that the modular motor 250 is removed as a unit from the base 234 along a slot 260 in a direction away from the diagnostic system so as to move the modular motor away from the attractive magnetic field generated by the MR scanner 216. The slot 260 ensures that the modular motor 250 can be grasped and pulled in the general direction away from the MR scanner magnet without pinching the grasping hand.

With reference to FIGS. 23-25, in some embodiments a bayonet-and-keyhole arrangement is used to ensure that the modular motor 250 is drawn generally away from an attractive magnetic field generated by the MR scanner 216. The modular motor has a bottom surface 266 including bayonets 270 that insert into keyholes 272 of a plate 274 of the base 234. (Alternatively, the bayonets can be disposed on the base and the keyholes or key-slots disposed on the motor). FIG. 24 shows the locked position, in which the bayonets 270 are in the narrow portion of the keyholes 272. The arrangement is such that the force imposed by the MR scanner magnet on the motor 250 (indicated by arrow "$F_{magnet}$" in FIGS. 24 and 25) tends to keep the modular motor 250 in the locked position of FIG. 24. FIG. 25 shows the unlocked position, achieved by a person applying a removal force to the motor 250 (indicated by arrow "$F_{removal}$" in FIG. 25 operating on the motor 250) that is opposite to and greater than the magnet force. The removal force ($F_{removal}$) moves the bayonets 270 over to the wide portion of the keyholes 272. In this unlocked position of FIG. 25, the modular motor 250 can be lifted up away from the base 234 as shown, for example, in FIG. 20, since the heads of the bayonets 270 can pass through the wide portion of the keyholes 272. Instead of the illustrated bayonet-and-keyhole arrangement, another linearly actuated quick-release coupling having suitable release directionality can be used. The slot 260 provides sufficient room for grasping the modular motor 250 to pull it away from the magnet and up without pinching of the grasping hand or fingers.

The directional quick release coupling 270, 272 ensures that the motor is drawn away from the attractive magnetic force $F_{magnet}$. This reduces the likelihood of the motor being drawn toward the MR scanner 216. Additionally, this arrangement provides the person removing the motor with notice of the attractive magnetic force $F_{magnet}$, since the person must pull the motor (that is, exert the removal force $F_{removal}$) against the resistance of the magnetic force $F_{magnet}$.

For an isolation environment such as BSL-4, the illustrated example subject tables 30, 130, 230 are optionally designed to be disassembled or repaired using a single tool. For example, all user-accessible components can be secured using a screw having a single type of head that is operable using a common screwdriver. Rather than screws, other standardized detachable fasteners such as bolts can also be used. The subject tables 30, 130, 230 optionally have a quick-release top pallet (e.g., the top elongated tabletop or pallet 42 of the table 30, or the tabletop or pallet 142 of the table 130, or the tabletop or pallet 242 of the table 230) which facilitates removal of the pallet and access to underlying components for sterilization, replacement, or maintenance. Such quick-release pallets can also be rapidly detached from the motorized drive to facilitate emergency manual extraction of the pallet (and hence the subject) from the tube 20.

The subject tables 30, 130, 230 optionally have a high degree of modularity to facilitate bagging and rapid replacement of components in the isolation zone 10. For example, the drive motors 48, 52, 250 can be removed as a unit and bagged for decontamination, and a replacement modular drive motor installed. Moreover, the bottom and top drive motors 48, 52 of the subject table 30 are optionally interchangeable to reduce the inventory of replacement motors that are kept in the isolation zone 10. In some embodiments, the mechanical drives are highly modular, so that for example in some embodiments the gearing assembly and driveshaft of each motorized drive 46, 50 of the subject table 30 can be installed and removed as a unit.

The subject tables 30, 130, 230 are suitably made of stainless steel, Teflon coated fasteners, and other exposed components that are resistant to decontamination chemicals used in decontaminating the isolation zone 10. In the case of a BSL-4 isolation zone 10, for example, the exposed components of the subject tables 30, 130, 230 should be resistant to chemicals including at least Clydox-S, Microchem, Quat TB, Para-Formaldehyde, Chlorine-Dioxide, Vaporized Hydrogen Peroxide, and Ammonium Carbonate, which are chemicals typically used in decontamination of a BSL-4 environment. On the other hand, internal components of sealed units, such as the internal components of the modular motor 250, are optionally less resistant to such chemicals, and may include materials or substances such as lubricants that are generally not favored in the BSL-4 environment.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A subject loading system for moving a subject disposed in an isolation zone into and out of a diagnostic system disposed outside the isolation zone, the subject insertion system comprising:
    a tube extending away from the isolation zone, the tube having an inner volume open to the isolation zone and operatively coupled with the diagnostic system;
    an elongated subject support pallet disposed in the isolation zone and dimensioned to fit into the tube; and
    a base, secured to a floor, including a mechanical drive disposed in the isolation zone and configured to align the elongated subject support pallet with the tube and to move the elongated subject support pallet into and out of the tube.

2. The subject loading system as set forth in claim 1, wherein the tube is one of cylindrical and tapered and has a cross section selected from the group consisting of circular and elliptical.

3. The subject loading system as set forth in claim 1, wherein the tube comprises at least one of: (i) a non-magnetic material compatible with magnetic resonance scanning, (ii) a material substantially transparent to x-rays generated during transmission computed tomography scanning or x-ray imaging, and (iii) a material substantially transparent to 511 keV gamma rays generated by positron electron annihilation events.

4. The subject loading system as set forth in claim 1, wherein the base and the mechanical drive are configured to support the elongated subject support pallet cantilevered from an end of the base proximate to the tube when the elongated subject support pallet is at least partially extended into the tube.

5. The subject loading system as set forth in claim 1, wherein the elongated subject support pallet is supported by a lower surface of the tube when the elongated subject support pallet is at least partially extended into the tube.

6. The subject loading system as set forth in claim 1, wherein the base includes:
    a front support pillar secured to a floor or platform in the isolation zone and movably engaged with the elongated subject support pallet; and
    a rear support pillar secured to an end of the elongated subject support pallet distal from the tube and movably engaged with the floor or platform in the isolation zone.

7. The subject loading system as set forth in claim 6, further including:
    a rubber strip seal substantially sealing a slot in a mechanical drive cover along which the rear support pillar moves.

8. The subject loading system as set forth in claim 1, wherein the elongated subject support pallet includes:
    an elongated intermediate pallet movably engaged with the base to move at least partially into the tube; and
    an elongated top pallet disposed on the elongated intermediate pallet and movably engaged with the elongated intermediate pallet to extend further into the tube than the elongated intermediate pallet.

9. The subject loading system as set forth in claim 8, wherein the elongated intermediate pallet includes:
    a top motorized mechanical drive for driving the extending of the elongated top pallet further into the tube, the top motorized mechanical drive including a hermetically sealed modular motor removable as a hermetically sealed unit from the top motorized mechanical drive.

10. The subject loading system as set forth in claim 9, wherein the base includes:
a bottom motorized mechanical drive including a hermetically sealed modular motor removable as a hermetically sealed unit from the bottom motorized mechanical drive.

11. The subject loading system as set forth in claim 10, wherein the modular motors of the bottom and top motorized mechanical drives are interchangeable.

12. The subject loading system as set forth in claim 10, wherein the bottom motorized mechanical drive is interlocked such that the elongated intermediate pallet cannot be moved out of the tube unless the elongated top pallet is in a retracted position.

13. The subject loading system as set forth in claim 8, further including:
an engagement element disposed in the tube to engage and stop forward insertion of the elongated intermediate pallet into the tube.

14. The subject loading system as set forth in claim 13, wherein the engagement element is aligned with a tube support disposed outside the isolation zone such that the tube supports the engagement element at the position of the tube support.

15. The subject loading system as set forth in claim 1, wherein the base includes:
a motorized mechanical drive including a hermetically sealed modular motor removable as a hermetically sealed unit from the motorized mechanical drive.

16. The subject loading system as set forth in claim 1, wherein the elongated subject support pallet and the base are resistant to decontamination chemicals used in decontaminating the isolation zone.

17. The subject loading system as set forth in claim 1, further including:
a movable engagement between the diagnostic system and a platform or floor supporting the diagnostic system outside the isolation zone, the movable engagement enabling the diagnostic system to be linearly moved along the tube between an operative position and a maintenance position.

18. The subject loading system as set forth in claim 1, wherein the mechanical drive of the base is a motorized mechanical drive including a modular motor removable as a unit from the base.

19. The subject loading system as set forth in claim 18, wherein the base includes a slot, the modular motor being removed as a unit from the base along the slot in a direction away from the diagnostic system so as to move the modular motor generally away from an attractive magnetic field generated by the diagnostic system.

20. The subject loading system as set forth in claim 18, wherein the modular motor is sealed to enable decontamination as a sealed unit.

21. The subject loading system as set forth in claim 1, wherein the mechanical drive of the base includes:
a hand brake having an "on" setting that prevents movement of the elongated subject support pallet and an "off" setting that allows movement of the elongated subject support pallet.

22. A subject support table comprising:
a subject support pallet;
a front support pillar secured to a floor or platform and movably engaged with the subject support pallet;
a rear support pillar secured to the subject support pallet and movably engaged with the floor or platform;
a motorized drive engaging the rear support pillar to move the rear support pillar respective to the front support pillar so as to move the subject support pallet across the front support pillar; and
a rubber strip seal substantially sealing a slot in a motorized drive cover that covers the motorized drive, the rear support pillar moving along the slot.

23. The subject support table as set forth in claim 22, wherein the motorized drive is disposed on or in the floor or platform.

24. The subject support table as set forth in claim 22, wherein the motorized drive includes:
a modular motor removable as a unit from the motorized drive.

25. The subject support table as set forth in claim 22, wherein the motorized drive includes:
a hermetically sealed modular motor removable as a hermetically sealed unit from the motorized drive.

26. The subject support table as set forth in claim 22, wherein the subject support pallet includes:
an intermediate pallet movably engaged with the front subject support pillar and secured to the rear support pillar; and
a top pallet disposed on and movably engaged with the intermediate pallet.

27. A subject loading system for moving a subject disposed in an isolation zone into and out of a diagnostic system disposed outside the isolation zone, the subject insertion system comprising:
a tube at an elevated height above a floor of the isolation zone, the tube at the elevated height above the floor extending away from the isolation zone and having an inner volume open to the isolation zone and overlapping an imaging region of the diagnostic system;
an elongated subject support pallet disposed in the isolation zone and sized to fit into the tube at the elevated height above the floor; and
a base including a mechanical drive disposed in the isolation zone and configured to align the elongated subject support pallet with the tube at the elevated height above the floor and to move the elongated subject support pallet into and out of the tube at the elevated height above the floor.

28. The subject loading system as set forth in claim 27, further comprising:
a barrier wall disposed between the isolation zone and the diagnostic system, the barrier wall at least contributing to fluid isolation of the diagnostic system from the isolation zone, the barrier wall having an opening at the elevated height above the floor;
wherein the tube at the elevated height above the floor has an open end mating with and sealing the opening at the elevated height in the barrier wall, the inner volume of the tube at the elevated height above the floor being open to the isolation zone via the opening at the elevated height in the barrier wall.

29. The subject loading system as set forth in claim 27, wherein the tube at the elevated height above the floor has a cross-section sized to coincide with a bore of the diagnostic system.

* * * * *